(12) United States Patent
Mirkin et al.

(10) Patent No.: US 9,677,075 B2
(45) Date of Patent: Jun. 13, 2017

(54) METAL-LIGAND COORDINATION POLYMER NANOPARTICLES AND METHODS FOR MAKING

(71) Applicant: NORTHWESTERN UNIVERSITY, Evanston, IL (US)

(72) Inventors: Chad A. Mirkin, Wilmette, IL (US); Colin Michael Calabrese, Evanston, IL (US); William Morris, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/786,569

(22) PCT Filed: Apr. 23, 2014

(86) PCT No.: PCT/US2014/035158
§ 371 (c)(1),
(2) Date: Oct. 23, 2015

(87) PCT Pub. No.: WO2015/012916
PCT Pub. Date: Jan. 29, 2015

(65) Prior Publication Data
US 2016/0068839 A1 Mar. 10, 2016

Related U.S. Application Data

(60) Provisional application No. 61/815,155, filed on Apr. 23, 2013, provisional application No. 61/871,170, filed on Aug. 28, 2013, provisional application No. 61/973,722, filed on Apr. 1, 2014.

(51) Int. Cl.
| | | |
|---|---|---|
| *A01N 43/04* | (2006.01) | |
| *A61K 31/70* | (2006.01) | |
| *C12N 15/113* | (2010.01) | |
| *G01N 33/543* | (2006.01) | |
| *C07H 21/00* | (2006.01) | |
| *C07F 9/58* | (2006.01) | |
| *C07F 15/02* | (2006.01) | |
| *C12Q 1/68* | (2006.01) | |
| *A61K 31/7052* | (2006.01) | |
| *A61K 31/7088* | (2006.01) | |
| *B82Y 5/00* | (2011.01) | |

(52) U.S. Cl.
CPC ............ *C12N 15/113* (2013.01); *C07F 9/581* (2013.01); *C07F 15/02* (2013.01); *C07H 21/00* (2013.01); *C12Q 1/68* (2013.01); *G01N 33/54346* (2013.01); *A61K 31/7052* (2013.01); *A61K 31/7088* (2013.01); *B82Y 5/00* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh Dinh et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,367,066 A | 11/1994 | Urdea et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 7,223,833 B1 | 5/2007 | Nielsen et al. |
| 2011/0104213 A1 | 5/2011 | Rosi et al. |
| 2012/0283410 A1 | 11/2012 | Mirosevich et al. |

FOREIGN PATENT DOCUMENTS

| | | |
|---|---|---|
| EP | 1072679 A2 | 1/2001 |
| WO | WO-97/12896 A1 | 4/1997 |
| WO | WO-2007/047455 A2 | 4/2007 |

OTHER PUBLICATIONS

Altschul et al., Basic local alignment search tool, J. Mol. Biol., 215(3):403-10 (1990).
Burgess et al., Hydroxypyranones, hydroxypyridinones, and their complexes, Adv. Inorg. Chem., 60:167-243 (2008).
Cavka et al., A new zirconium inorganic building brick forming metal organic frameworks with exceptional stability, J. Am. Chem. Soc., 130(42):13850-1 (2008).
Chen et al., Metal-organic frameworks-based biosensor for sequence-specific recognition of double-stranded DNA, 138(12):3490-3 (2013).
Choi et al., Synthesis of DNA triangles with vertexes of bis(terpyridine)iron(II) complexes, J. Am. Chem. Soc., 126(28):8606-7 (2004).
Crawford et al., Peptide aptamers: Tools for biology and drug discovery. 2(1): 72-9 (2003).
Cutler et al., Spherical nucleic acids, J. Am. Chem. Soc., 134(3):1376-91 (2012).
Ehrenschwender et al., Metal-mediated DNA assembly using the ethynyl linked terpyridine ligand, Org. Biomol. Chem., 10(1):46-8 (2012).
Englisch et al., Chemically modified oligonucleotides as probes and inhibitors, Ang. Chem. Int. Ed., 30:613-29 (1991).
Freier et al., The ups and downs of nucleic acid duplex stability: structure-stability studies on chemically-modified DNA:RNA duplexes, Nucleic Acids Res., 25:4429-43 (1997).
Gordon et al., Reactivity of biarylazacyclooctynones in copper-free click chemistry, J. Am. Chem. Soc., 134(22):9199-208 (2012).

(Continued)

Primary Examiner — Patrick Lewis
(74) Attorney, Agent, or Firm — Marshall, Gerstein & Borun LLP

(57) ABSTRACT

Disclosed herein are metal-ligand complexes containing polynucleotides, compounds for making the same, and methods of using the same.

9 Claims, 9 Drawing Sheets

(56) References Cited

OTHER PUBLICATIONS

He et al., Nanoscale metal-organic frameworks for the co-delivery of cisplatin and pooled siRNAs to enhance therapeutic efficacy in drug-resistant ovarian cancer cells, J. Am. Chem. Soc., 136(14):5181-4 (2014).

International Preliminary Report on Patentability, International Application No. PCT/US2014/035158, dated Oct. 27, 2015.

International Search Report and Written Opinion, International Application No. PCT/US2014/035158, mailed Feb. 13, 2015.

Katz, The reversible reaction of sodium thymonucleate and mercuric chloride, J. Am. Chem. Soc., 74:2238-45 (1951).

Kopylov et al., Combinatorial chemistry of nucleic acids: SELEX, Mol. Biol., 34: 940-54 (2000).

Kosturko et al., The crystal and molecular structure of a 2:1 complex of 1-methylthymine-mercury(II), Biochemistry, 13:3949-52 (1974).

Kroschwitz (ed.), *The Concise Encyclopedia of Polymer Science and Engineering*, pp. 858-859, New York: John Wiley & Sons (1990).

Liu et al., Design of iron chelators with therapeutic application, Coord. Chem. Rev., 232(1-2):151-71 (2002).

Megger et al., Metal-mediated aggregation of DNA comprising 2,2'-bipyridine nucleoside, an asymmetrically substituted chiral bidentate ligand, Dalton Trans., 40(8):1802-7 (2011).

Mitchell et al., Chemical tags mediate the orthogonal self-assembly of DNA duplexes into supramolecular structures, Small, 6(16):1732-5 (2010).

Saghaie et al., Synthesis, analysis and determination of partition coefficients of N-arylhydroxypyridinone derivatives as iron chelators, Res. Pharm. Sci., 1:40-8 (2006).

Sanghvi, Heterocyclic base modifications in nucleic acids and their applications in antisense oligonucleotides, Chapter 15 in Crooke et al. (eds.), *Antisense Research and Applications*, CRC Press (1993).

Schlegel et al., Metal-mediated base pairing within the simplified nucleic acid GNA, Org. Biomol. Chem., 7(3):476-82 (2009).

Takezawa et al., Discrete self-assembly of iron(III) ions inside triple-stranded artificial DNA, Angew. Chem. Int. Ed. Engl., 48(6):1081-4 (2009).

Tanaka et al., Efficient incorporation of a copper hydroxypyridone base pair in DNA, J. Am. Chem. Soc., 124(42):12494-8 (2002).

Thomas, The interaction of $HgCl_2$ with sodium thymonucleate, J. Am. Chem. Soc., 76:6032-4 (1954).

Tuerk et al., Systematic evolution of ligands by exponential enrichment: RNA ligands to bacteriophage T4 DNA polymerase. Science, 249: 505-10 (1990).

Yamane et al., On the complexing of desoxyribonucleic acid (DNA) by mercuric ion, J. Am. Chem. Soc., 83:2599-607 (1961).

Yan et al., Aptamers and aptamer targeted delivery. RNA Biol., 6: 316-20 (2009).

Zhang et al., An extremely stable and orthogonal DNA base pair with a simplified three-carbon backbone, J. Am. Chem. Soc., 127:74-5 (2005).

Zhang et al., PowerBlast: A new network BLAST application for interactive or automated sequence analysis and annotation. Genome, 7: 649-56 (1997).

Zimmerman et al., "A novel silver(I)-mediated DNA base pair," J. Am. Chem. Soc., 124:13684-13685 (2002).

$d_{avg}$ (AFM) 31.5 nm; $d_{avg}$ (DLS) 32.2 nm

METAL-LIGAND COORDINATION POLYMER NANOPARTICLES AND METHODS FOR MAKING

CROSS REFERENCE TO RELATED APPLICATIONS

This application claims the priority benefit under 35 U.S.C. §119(e) of U.S. Provisional Application No. 61/815,155, filed Apr. 23, 2013, U.S. Provisional Application No. 61/871,170, filed Aug. 28, 2013, and U.S. Provisional Application No. 61/973,722, filed Apr. 1, 2014, the disclosures of which are incorporated herein by reference in their entirety.

STATEMENT OF U.S. GOVERNMENT SUPPORT

This invention was made with government support under grant number HR0011-13-2-0018 awarded by the Defense Advanced Research Projects Agency Microsystems Technology Office (DARPA/MTO), grant number U54 CA151880 awarded by the National Institutes of Health, grant number W911NF-11-1-0229 awarded by the Army Research Office (ARO), grant number N66001-11-1-4189 awarded by the Space and Naval Warfare Systems Center (DARPA/MTO Award), grant number FA9550-11-1-0275 awarded by The Air Force Office of Scientific Research (AFOSR), and grant number FA9550-12-1-0280 awarded by The Air Force Office of Scientific Research (AFOSR). The government has certain rights in the invention.

BACKGROUND

Field of the Invention

The disclosure generally relates to metal-ligand complexes containing polynucleotides, compounds for making the same, and methods of using the same.

Brief Description of Related Technology

Metal-organic complexes include metal-ligand chelation complexes such as the family of bidentate iron chelators known as 3-hydroxy-4-pyridinones (3,4-HOPOs), which are highly specific ligands for iron (III). This specificity allows iron to be complexed in the presence of DNA, which itself has intrinsic affinity for iron. Deferiprone (1,2-dimethyl-3-hydroxy-4-pyridinone), for example, is a 3,4-HOPO that is FDA-approved for the treatment of patients suffering from iron overload.

Metal-organic complexes also include metal-organic frameworks (MOFs), a large class of porous crystalline materials comprising metal/metal oxide units linked by organic ligands. MOF crystallite size can be controlled on the nanoscale, and post-modification can be used to functionalize the pores of MOFs.

Described herein are compounds and methods for constructing supramolecular assemblies containing 3,4-HOPOs conjugated to oligonucleotides. Also described herein are compounds and methods for constructing MOFs functionalized with oligonucleotides.

SUMMARY

The present disclosure is directed to metal-ligand complexes containing polynucleotides, compounds for making the same, and methods of using the same.

In one aspect, the present disclosure provides a compound having a structure:

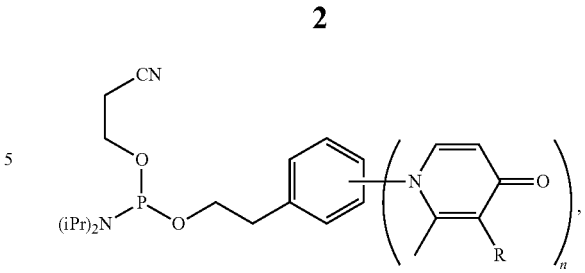

wherein R is OH or —O—C(O)—NAr$_2$, each Ar is aryl, and n is 1 or 2.

In a related aspect, the present disclosure provides a polynucleotide comprising at a terminus a moiety comprising:

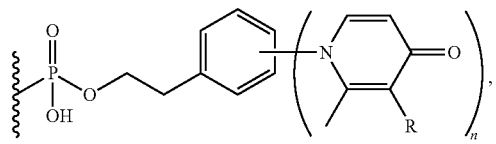

wherein R is OH or —O—C(O)—NAr$_2$, each Ar is aryl, and n is 1 or 2.

In another aspect, the present disclosure provides a polynucleotide comprising at a terminus a moiety comprising:

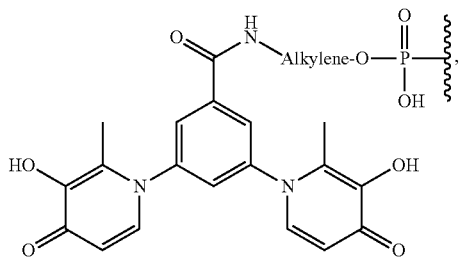

wherein Alkylene comprises 6-20 carbons.

In various aspects, the present disclosure provides a metal-ligand complex comprising a polynucleotide as described herein and iron (III).

In various aspects, the present disclosure provides a supramolecular complex comprising a first metal-ligand complex as described herein and a second metal-ligand complex as described herein, wherein the first metal-ligand complex comprises a first polynucleotide and the second metal-ligand complex comprises a second polynucleotide that is sufficiently complementary to the first polynucleotide to hybridize under appropriate conditions.

In various aspects, the present disclosure provides a method of inhibiting expression of a gene product encoded by a target polynucleotide comprising contacting the target polynucleotide with a supramolecular complex as described herein under conditions sufficient to inhibit expression of the gene product. In various aspects, the present disclosure also provides a method of detecting a target molecule comprising contacting the target molecule with a supramolecular complex as described herein, wherein contact between the target molecule and the supramolecular complex results in a detectable change.

In another aspect, the present disclosure provides a nanoparticle comprising a metal-organic framework and a plurality of polynucleotides attached to a surface of the metal-organic framework.

In a related aspect, the present disclosure provides a method for making a nanoparticle as described herein. The method comprises reacting (a) a metal-organic framework comprising (i) a metal and (ii) an organic ligand comprising a first functional group and (b) a polynucleotide comprising a linker having a second functional group. The first functional group and the second functional group react to form a covalent bond.

In various aspects, the present disclosure provides a method of inhibiting expression of a gene product encoded by a target polynucleotide comprising contacting the target polynucleotide with a nanoparticle as described herein under conditions sufficient to inhibit expression of the gene product. In various aspects, the present disclosure also provides a method of detecting a target molecule comprising contacting the target molecule with a nanoparticle as described herein, wherein contact between the target molecule and the nanoparticle results in a detectable change.

These and other embodiments and features of the present invention will become apparent from the following detailed description of the preferred embodiments.

DETAILED DESCRIPTION

Figure 1A:
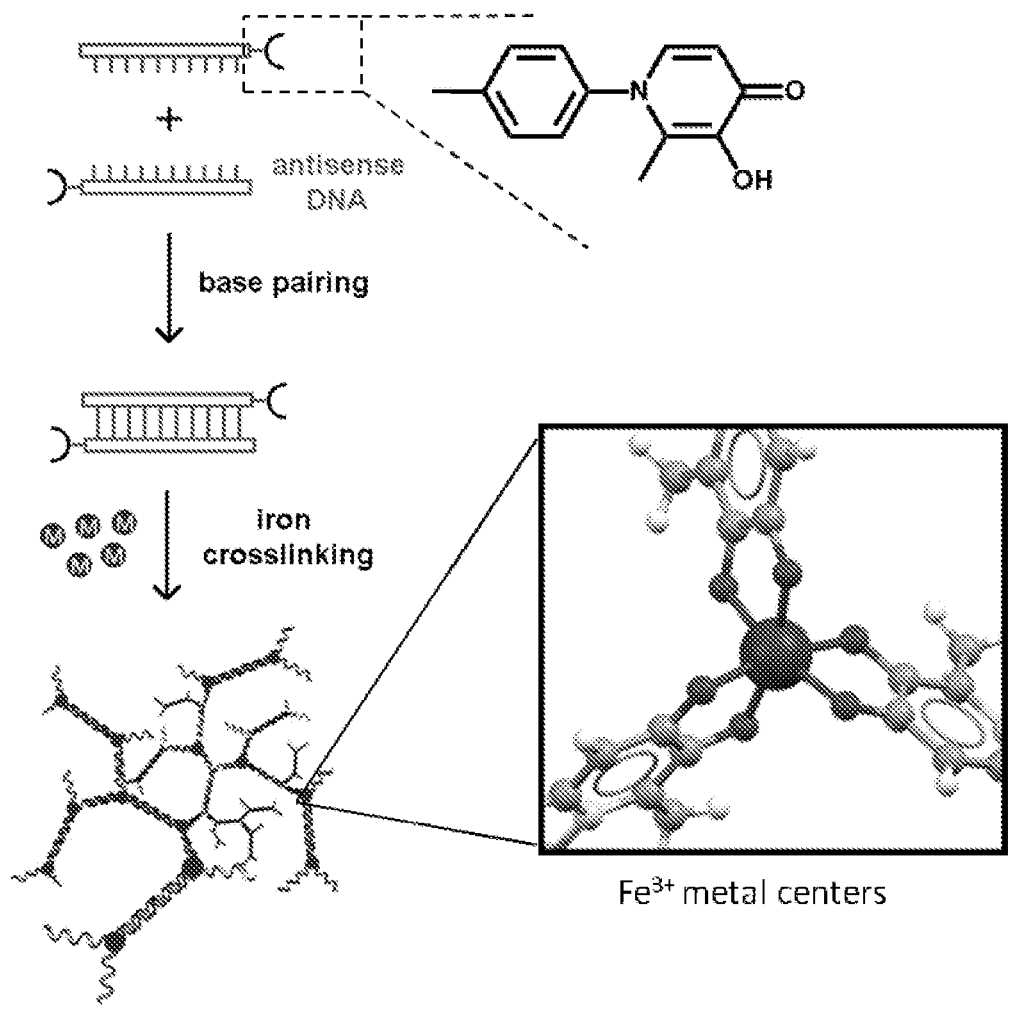
FIG. 1A is a schematic diagram showing formation of supramolecular complexes.

The present disclosure is directed to metal-ligand complexes containing polynucleotides, compounds for making the same, and methods of using the same.

It is noted here that, as used in this specification and the appended claims, the singular forms "a," "an," and "the" include plural reference unless the context clearly dictates otherwise.

It is also noted that the term "about" as used herein is understood to mean approximately.

As used herein, the term "alkyl" refers to straight chained and branched hydrocarbon groups, nonlimiting examples of which include methyl, ethyl, and straight chain and branched propyl and butyl groups. The term "alkyl" includes "bridged alkyl," i.e., a bicyclic or polycyclic hydrocarbon group, for example, norbornyl, adamantyl, bicycle[2.2.2]octyl, bicyclo [2.2.1]heptyl, bicyclo[3.2.1]octyl, or decahydronaphthyl. Alkyl groups optionally can be substituted, for example, with hydroxy (OH), halo, aryl, heteroaryl, ester, carboxylic acid, amido, guanidine, and amino. The term "alkylene" refers to an alkyl group that is substituted. For example, an alkylenehydroxy group is an alkyl group having a hydroxy group somewhere on the alkyl.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

Metal-Ligand Coordination Polymer Nanoparticles

The present disclosure provides phosphoramidite ligand precursors that contain a phosphoramidite moiety and a ligand or ligand precursor moiety. Phosphoramidite moieties have a general formula $(R^1O)_2PN(R^2)_2$, wherein each of the $R^1$ groups is typically a substituted alkyl group (e.g., one of the $R^1$ groups is a cyanoethyl group) and each of the $R^2$ groups is typically an alkyl group such as a $C_{1-4}$ alkyl group (e.g., an isopropyl group). The phosphoramidite moiety allows the phosphoramidite ligand precursor to be incorporated into a polynucleotide using typical polynucleotide synthesis procedures, including automated oligonucleotide synthesis procedures. The ligand or ligand precursor moiety includes 3-hydroxy-4-pyridinone moieties and protected versions thereof.

In one aspect, the present disclosure provides a phosphoramidite ligand precursor having a structure:

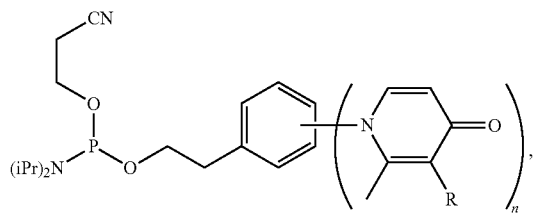

wherein R is OH or —O—C(O)—NAr$_2$, each Ar is aryl, and n is 1 or 2. In some embodiments, each Ar is the same. In some embodiments, at least one Ar is phenyl. In various embodiments, a pyridone moiety is attached to the phenyl moiety at the para position. In various embodiments, one or two pyridone moieties are attached to the phenyl moiety at the meta position(s).

Phosphoramidite ligand precursors can be attached to polynucleotides using typical polynucleotide synthesis procedures to obtain polynucleotides containing ligands or ligand precursors. In one aspect, the present disclosure provides a polynucleotide comprising at a terminus a moiety comprising:

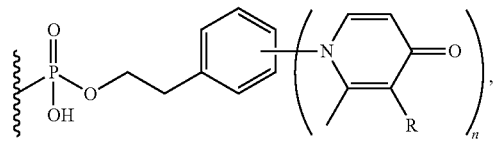

wherein R is OH or —O—C(O)—NAr$_2$, each Ar is aryl, and n is 1 or 2. In some embodiments, each Ar is the same. In some embodiments, at least one Ar is phenyl. In various embodiments, a pyridone moiety is attached to the phenyl moiety at the para position. In various embodiments, one or two pyridone moieties are attached to the phenyl moiety at the meta position(s).

Polynucleotides containing ligands or ligand precursors can also be obtained by attaching the ligands or ligand precursors to polynucleotides modified to have reactive functional groups. For example, an aminoalkyl-modified polynucleotide can be attached to a ligand or ligand precursor having a carboxylic acid group or an activated carboxylic acid group. Suitable reagents for activating carboxylic acid groups include, but are not limited to, carbodiimides (e.g., dicyclohexylcarbodiimide, diisopropylcarbodiimide, 1-ethyl-3-[3-dimethylaminopropyl]carbodiimide, phenyl ethyl carbodiimide, phenyl isopropyl carbodiimide), benzotriazoles (e.g., 1-hydroxy-1H-benzotriazole, 1-hydroxy-7-azabenzotriazole, O-(7-azabenzotriazol-1-yl)-1,1,3,3-tetramethyluronium hexafluorophosphate, O-(benzotriazol-1-yl)-1,1,3,3-tetramethyluronium hexafluorophosphate), and mixtures thereof.

In one aspect, the present disclosure provides a polynucleotide comprising at a terminus a moiety comprising:

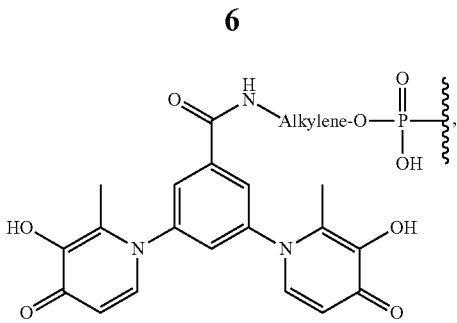

wherein Alkylene comprises 6-20 carbons. Alkylene groups include, but are not limited to, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, —(CH$_2$)$_{19}$—, and —(CH$_2$)$_{20}$—.

In various aspects, the present disclosure provides a metal-ligand complex comprising a polynucleotide as described herein and iron (III). In some embodiments, the metal-ligand complex comprises iron (III) and a polynucleotide comprising at a terminus a moiety comprising:

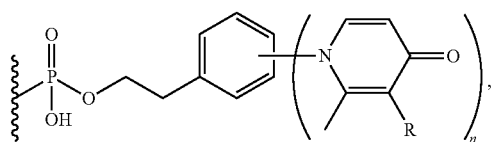

wherein R is OH or —O—C(O)—NAr$_2$, each Ar is aryl, and n is 1 or 2. For example, in some embodiments, the metal-ligand complex comprises iron (III) and a polynucleotide comprising at a terminus a moiety comprising:

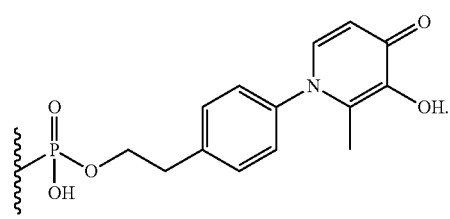 [SMILES: *P(=O)(O)OCCc1ccc(-n2ccc(=O)c(O)c2C)cc1]

In some embodiments, the metal-ligand complex comprises iron (III) and a polynucleotide comprising at a terminus a moiety comprising:

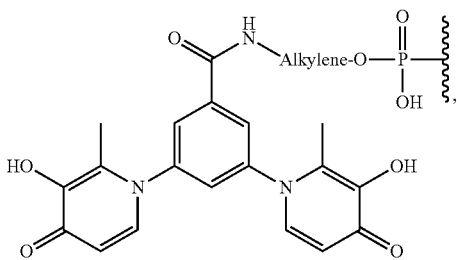

wherein Alkylene comprises 6-20 carbons. In some embodiments the metal-ligand complex has three polynucleotides (PN) for every iron (III) ion (e.g., Fe(PN)$_3$). In some embodiments the metal-ligand complex has three ligands for every iron (III) ion.

The metal-ligand complex typically is prepared by combining a solution of a ligand-modified polynucleotide as described herein with a solution of $Fe^{3+}$ in a suitable solvent. Generally, the molar ratio of $Fe^{3+}$ to polynucleotide when combined in the solvent is at least 1:10, for example, at least 1:5, at least 1:3, at least 1:2, at least 1:1.5, at least 1:1, at least 1:0.75, at least 1:0.5, at least 1:0.25, and/or at least 1:0.1. Suitable solvents include, but are not limited to, water and aqueous buffer solutions such as phosphate buffered saline. Generally, the pH of the solvent is about 6 to about 11, for example, about 7 to about 10, about 7 to about 9, and/or about 7 to about 8.

In various aspects, the present disclosure provides a supramolecular complex comprising a first metal-ligand complex as described herein and a second metal-ligand complex as described herein, wherein the first metal-ligand complex comprises a first polynucleotide and the second metal-ligand complex comprises a second polynucleotide that is sufficiently complementary to the first polynucleotide to hybridize under appropriate conditions. In various embodiments, the supramolecular complex comprises the first polynucleotide hybridized with the second polynucleotide. In some embodiments, the melting temperature ($T_m$) of the hybridized first and second polynucleotides is at least about 30° C., at least about 35° C., at least about 40° C., at least about 45° C., at least about 50° C., at least about 55° C., at least about 60° C., at least about 65° C., at least about 70° C., at least about 75° C., at least about 80° C., at least about 85° C., at least about 90° C., at least about 95° C., and/or at least about 100° C. The supramolecular complexes typically are present as nanoparticles having an average particle diameter of about 1 nm to about 1000 nm, for example, about 2 nm to about 900 nm, about 3 nm to about 800 nm, about 4 nm to about 700 nm, about 5 nm to about 600 nm, about 5 nm to about 500 nm, about 5 nm to about 400 nm, about 5 nm to about 300 nm, about 5 nm to about 200 nm, about 10 nm to about 200 nm, about 10 nm to about 100 nm, about 10 nm to about 90 nm, about 10 nm to about 80 nm, about 10 nm to about 70 nm, about 10 nm to about 60 nm, about 10 nm to about 50 nm, about 20 nm to about 40 nm, and/or about 30 nm.

Supramolecular complexes typically are prepared by combining a solution of a first polynucleotide with a solution of a second polynucleotide in a suitable solvent to form a double-stranded polynucleotide monomer. The double-stranded polynucleotide monomer is then combined with a solution of $Fe^{3+}$ in a suitable solvent to form the supramolecular complex. Generally, the molar ratio of $Fe^{3+}$ to total polynucleotide when combined in the solvent is at least 1:10, for example, at least 1:5, at least 1:3, at least 1:2, at least 1:1.5, at least 1:1, at least 1:0.75, at least 1:0.5, at least 1:0.25, and/or at least 1:0.1. Suitable solvents include, but are not limited to, water and aqueous buffer solutions such as phosphate buffered saline. Generally, the pH of the solvent is about 6 to about 11, for example, about 7 to about 10, about 7 to about 9, and/or about 7 to about 8.

In various aspects, the present disclosure provides a method of inhibiting expression of a gene product encoded by a target polynucleotide comprising contacting the target polynucleotide with a supramolecular complex as described herein under conditions sufficient to inhibit expression of the gene product. In some embodiments, expression of the gene product is inhibited in vivo. In some embodiments, expression of the gene product is inhibited in vitro. In various embodiments, expression of the gene product is inhibited by at least about 5% relative to expression of the gene product in the absence of contacting the target polynucleotide with the supramolecular complex, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, and/or at least about 95%. In various aspects, the present disclosure also provides a method of detecting a target molecule comprising contacting the target molecule with a supramolecular complex as described herein, wherein contact between the target molecule and the supramolecular complex results in a detectable change. In some embodiments, the detecting is in vitro. In some embodiments, the detecting is in vivo.

Nucleic Acid-Metal Organic Framework (MOF) Nanoparticle Conjugates

Metal-organic frameworks (MOFs) are 1, 2, or 3-dimensional microporous materials containing metals/metal ions coordinated to organic ligands. As used herein, MOFs include infinite coordination polymers (ICPs), including, but not limited to, the ICPs disclosed in US Patent Application Publication No. 2009/0211445, which is incorporated herein by reference in its entirety.

The present disclosure provides a nanoparticle comprising a metal-organic framework and a plurality of polynucleotides attached to a surface of the metal-organic framework. The metal-organic framework comprises (1) a metal and (2) an organic ligand. In various embodiments, the metal-organic framework forms a nanoparticle core and the polynucleotides form a layer attached to an outer surface of the core. In various embodiments, the metal-organic framework has a three-dimensional structure. In various embodiments, the polynucleotides are attached to the metal-organic framework at a terminus of the polynucleotide. In various embodiments one terminus of the polynucleotide is attached to a surface of the metal-organic framework and the other terminus of the polynucleotide is oriented away from (or distal to) the surface of the metal-organic framework. In various embodiments, a linking group is covalently attached to both the metal-organic framework and the polynucleotide.

Suitable organic ligands include, but are not limited to, 1,2,4,5-tetrakis(4-carboxyphenyl)benzene, 1,3,5-tris(4'-carboxy[1,1'-biphenyl]-4-yl)benzene, 1,3,5-tris(4-carboxyphenyl)benzene, 2,5-dihydroxyterephthalic acid, 2,6-naphthalenedicarboxylic acid, 2-hydroxyterephthalic acid, 2-methylimidazole, 3,3',5,5'-tetracarboxydiphenylmethane, 4,4',4''-s-triazine-2,4,6-triyl-tribenzoic acid, 9,10-anthracenedicarboxylic acid, biphenyl-3,3',5,5'-tetracarboxylic acid, biphenyl-3,4',5-tricarboxylic acid, imidazole, terephthalic acid (i.e., 1,4-benzenedicarboxylic acid), trimesic acid, [1,1':4',1'']terphenyl-3,3',5,5'-tetracarboxylic acid, and derivatives thereof containing a functional group. Suitable functional groups include, but are not limited to, azides and alkynes. Suitable functional groups are capable of reacting with a paired functional group attached to a polynucleotide, thereby forming a covalent bond between the metal-organic framework and the polynucleotide. An exemplary pair of functional groups is an azide functional group and an alkyne functional group.

In some embodiments, the organic ligand comprises:

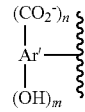

wherein Ar' is aryl, heteroaryl, or biphenyl; n is 1, 2, 3, or 4; and m is 0, 1, or 2.

In some embodiments, the organic ligand comprises:

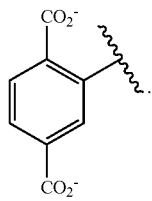

In some embodiments, the metal-organic framework comprises Ag, Al, Be, Ca, Cd, Ce, Co, Cr, Cu, Dy, Er, Eu, Fe, Ga, Gd, Ho, In, Li, Mg, Mn, Mo, Nd, Ni, Sc, Sm, Sr, Tb, Tm, V, W, Y, Yb, Zn, Zr, or mixtures thereof.

In various embodiments, the nanoparticle comprises a structure of formula (1A) or (2A):

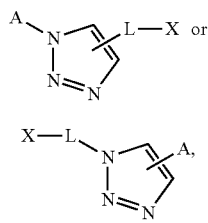

wherein A is an organic ligand of the metal-organic framework; L is a linking group; and X is the polynucleotide.

In some embodiments, the structure of formula (1A) comprises:

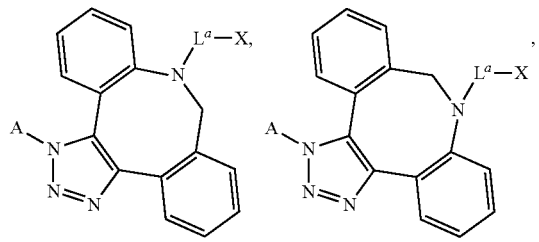

or a mixture thereof, wherein $L^a$ is a linking group. In some embodiments, $L^a$ is selected from the group consisting of $C_{1-10}$ alkylene, —C(O)—$C_{1-10}$ alkylene-Y—, and —C(O)—$C_{1-10}$ alkylene-Y—$C_{1-10}$ alkylene-(OCH$_2$CH$_2$)$_n$—Y—; wherein each Y is independently selected from the group consisting of a bond, C(O), O, NH, C(O)NH, and NHC(O); and n is 0, 1, 2, 3, 4, or 5.

In some embodiments, the structure of formula (1A) comprises:

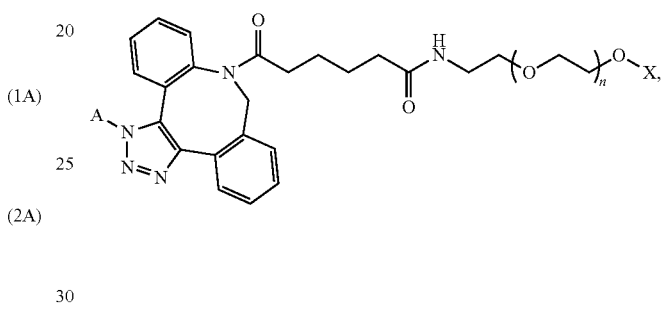

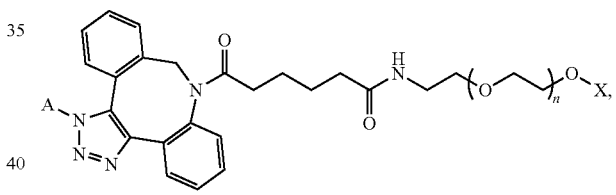

or a mixture thereof; wherein n is 0, 1, 2, 3, 4, or 5.

In some embodiments, the structure of formula (1A) comprises:

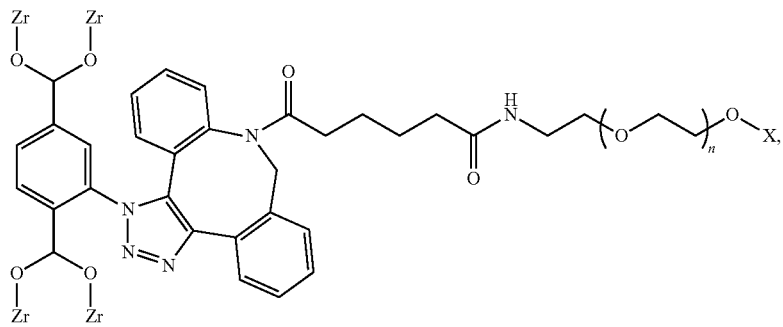

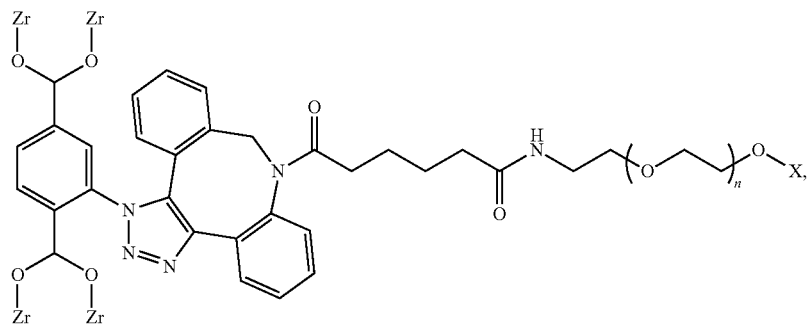
or a mixture thereof.
In some embodiments, the structure of formula (1A) comprises:
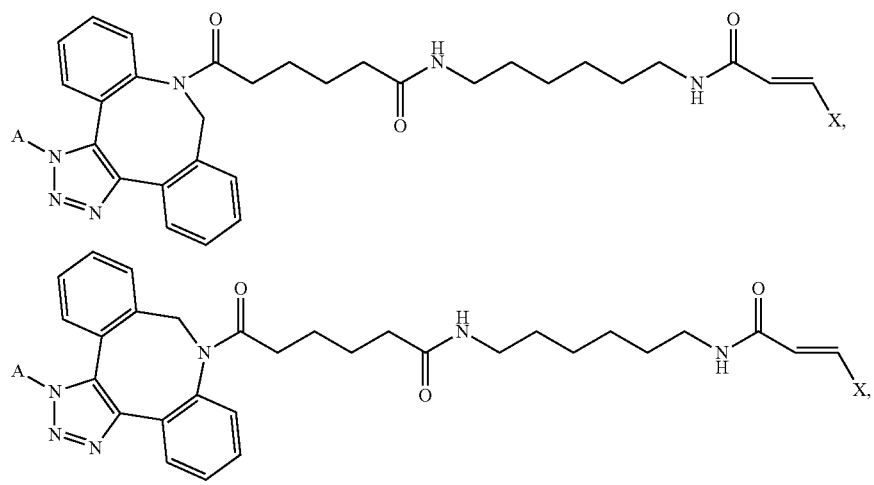
or a mixture thereof.
In some embodiments, the structure of formula (1A) comprises:
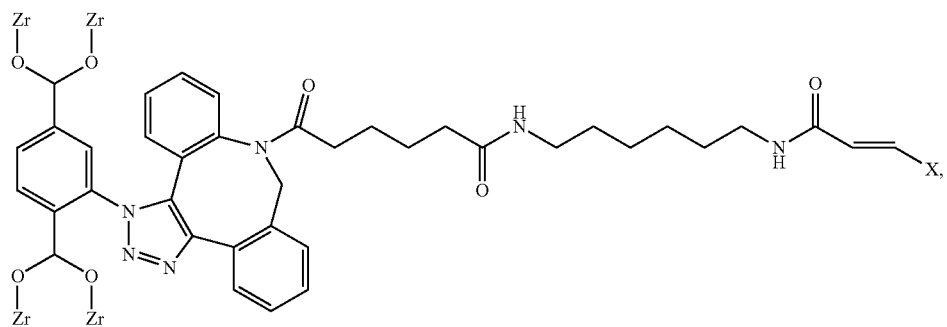

-continued

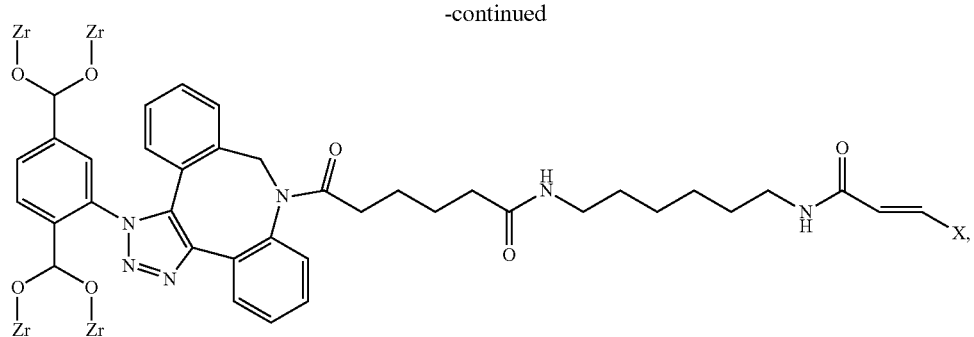

or a mixture thereof.

The nanoparticle comprising a metal-organic framework and a plurality of polynucleotides attached to a surface of the metal-organic framework is prepared by reacting (a) a metal-organic framework comprising (i) a metal and (ii) an organic ligand comprising a first functional group and (b) a polynucleotide comprising a linker having a second functional group. The first functional group and the second functional group react to form a covalent bond. In various embodiments, one of the first functional group and second functional group comprises an azide and the other comprises an alkyne, and the first functional group and the second functional group react to form a triazole. In some embodiments, the first functional group comprises the azide and the second functional group comprises the alkyne. In some embodiments, the first functional group comprises the alkyne and the second functional group comprises the azide.

In some embodiments, the organic ligand comprises:

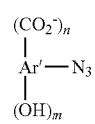

wherein Ar' is aryl, heteroaryl, or biphenyl; n is 1, 2, 3, or 4; and m is 0, 1, or 2.

In some embodiments, the organic ligand comprises:

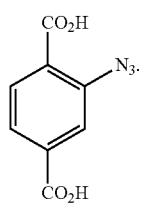

In some embodiments, the metal-organic framework comprises:

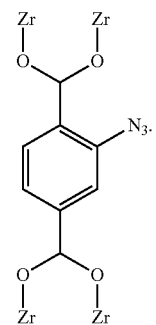

In some embodiments, the second functional group comprises the alkyne and the linker comprises a structure:

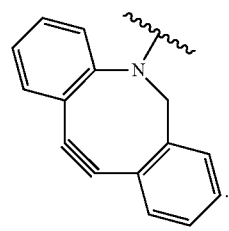 [SMILES: *N1Cc2ccccc2C#Cc2ccccc21]

In some embodiments, the second functional group comprises the alkyne and the linker comprises a structure:

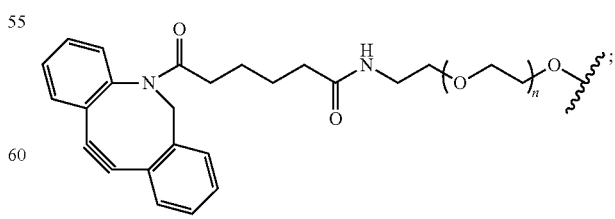

wherein n is 0, 1, 2, 3, 4, or 5; or the linker comprises a structure:

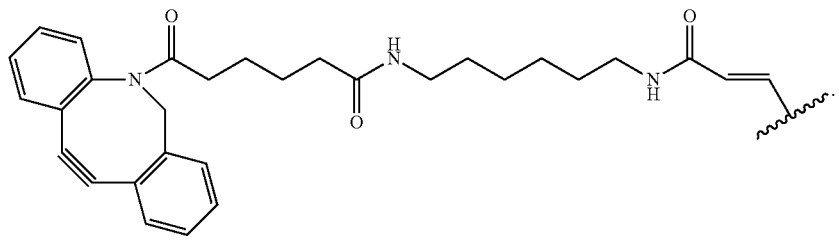 [SMILES: */C=C/C(=O)NCCCCCCNC(=O)CCCCC(=O)N1Cc2ccccc2C#Cc2ccccc21]

In various aspects, the present disclosure provides a method of inhibiting expression of a gene product encoded by a target polynucleotide comprising contacting the target polynucleotide with a nanoparticle as described herein under conditions sufficient to inhibit expression of the gene product. In some embodiments, expression of the gene product is inhibited in vivo. In some embodiments, expression of the gene product is inhibited in vitro. In various embodiments, expression of the gene product is inhibited by at least about 5% relative to expression of the gene product in the absence of contacting the target polynucleotide with the nanoparticle, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, and/or at least about 95%. In various aspects, the present disclosure also provides a method of detecting a target molecule comprising contacting the target molecule with a nanoparticle as described herein, wherein contact between the target molecule and the nanoparticle results in a detectable change. In some embodiments, the detecting is in vitro. In some embodiments, the detecting is in vivo.

Polynucleotides

Polynucleotides contemplated by the present disclosure include DNA, RNA, modified forms and combinations thereof as defined herein. Accordingly, in some aspects, the metal-ligand complex, supramolecular complex, or nanoparticle comprises DNA. In some embodiments, the DNA is double stranded, and in further embodiments the DNA is single stranded. In further aspects, the metal-ligand complex, supramolecular complex, or nanoparticle comprises RNA, and in still further aspects the metal-ligand complex, supramolecular complex, or nanoparticle comprises double stranded RNA, and in a specific embodiment, the double stranded RNA agent is a small interfering RNA (siRNA). The term "RNA" includes duplexes of two separate strands, as well as single stranded structures. Single stranded RNA also includes RNA with secondary structure. In one aspect, RNA having a hairpin loop in contemplated.

In some aspects, the polynucleotide is comprised of a sequence that is sufficiently complementary to a target sequence of a polynucleotide such that hybridization of the polynucleotide that is part of the metal-ligand complex, supramolecular complex, or nanoparticle and the target polynucleotide takes place. The polynucleotide in various aspects is single stranded or double stranded, as long as the double stranded molecule also includes a single strand sequence that hybridizes to a single strand sequence of the target polynucleotide. In some aspects, hybridization of the polynucleotide that is part of the metal-ligand complex, supramolecular complex, or nanoparticle can form a triplex structure with a double-stranded target polynucleotide. In another aspect, a triplex structure can be formed by hybridization of a double-stranded polynucleotide that is part of a metal-ligand complex, supramolecular complex, or nanoparticle to a single-stranded target polynucleotide. Further description of triplex polynucleotide complexes is found in PCT/US2006/40124, which is incorporated herein by reference in its entirety.

A "polynucleotide" is understood in the art to comprise individually polymerized nucleotide subunits. The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases adenine (A), guanine (G), cytosine (C), thymine (T) and uracil (U). Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-triazolopyridine, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleotides include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example, 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

The metal-ligand complexes, supramolecular complexes, and nanoparticles generally comprise a polynucleotide from about 5 nucleotides to about 100 nucleotides in length. More specifically, metal-ligand complexes, supramolecular complexes, and nanoparticles comprise polynucleotides that are about 5 to about 90 nucleotides in length, about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated.

Polynucleotides, as defined herein, also includes aptamers. The production and use of aptamers is known to those of ordinary skill in the art. In general, aptamers are nucleic acid or peptide binding species capable of tightly binding to and discreetly distinguishing target ligands (Yan et al., RNA Biol. 6(3) 316-320 (2009), incorporated by reference herein in its entirety). Aptamers, in some embodiments, may be obtained by a technique called the systematic evolution of ligands by exponential enrichment (SELEX) process (Tuerk et al., Science 249:505-10 (1990), U.S. Pat. No. 5,270,163, and U.S. Pat. No. 5,637,459, each of which is incorporated herein by reference in their entirety). General discussions of nucleic acid aptamers are found in, for example and without limitation, Nucleic Acid and Peptide Aptamers: Methods and Protocols (Edited by Mayer, Humana Press, 2009) and Crawford et al., Briefings in Functional Genomics and Proteomics 2(1): 72-79 (2003). Additional discussion of aptamers, including but not limited to selection of RNA aptamers, selection of DNA aptamers, selection of aptamers capable of covalently linking to a target protein, use of modified aptamer libraries, and the use of aptamers as a diagnostic agent and a therapeutic agent is provided in Kopylov et al., Molecular Biology 34(6): 940-954 (2000) translated from Molekulyarnaya Biologiya, Vol. 34, No. 6, 2000, pp. 1097-1113, which is incorporated herein by reference in its entirety. In various aspects, an aptamer is between 10-100 nucleotides in length.

In various aspects, the methods include use of a polynucleotide which is 100% complementary to the target polynucleotide, i.e., a perfect match, while in other aspects, the polynucleotide is at least (meaning greater than or equal to) about 95% complementary to the target polynucleotide over the length of the polynucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the target polynucleotide over the length of the polynucleotide to the extent that the polynucleotide is able to achieve the desired of inhibition of a target gene product. It will be understood by those of skill in the art that the degree of hybridization is less significant than a resulting detection of the target polynucleotide, or a degree of inhibition of gene product expression.

Polynucleotide Density

Nanoparticles as provided herein have a density of the polynucleotide on the surface of the nanoparticle. In some aspects, the resistance of the polynucleotide to degradation and/or the uptake of nanoparticles by a cell is influenced by the density of polynucleotides associated with the nanoparticle. As described in PCT/US2008/65366, incorporated herein by reference in its entirety, a higher density of polynucleotides on the surface of a polynucleotide functionalized nanoparticle is associated with an increased uptake of nanoparticles by a cell.

A surface density adequate to make the nanoparticles stable and the conditions necessary to obtain it for a desired combination of nanoparticles and polynucleotides can be determined empirically. Broadly, the smaller the polynucleotide that is used, the higher the surface density of that polynucleotide can be. Generally, a surface density of at least 1 pmol/cm$^2$ will be adequate to provide stable nanoparticle-compositions. In some aspects, the surface density is at least 10 pmol/cm$^2$. Methods are also provided wherein the polynucleotide is present in a nanoparticle at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^2$, at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more.

It is contemplated that the density of polynucleotides in a nanoconjugate modulates specific biomolecule and/or non-biomolecule interactions with the polynucleotide on the surface and/or with the nanoconjugate itself. Under various conditions, some polypeptides may be prohibited from interacting with polynucleotides that are part of a nanoconjugate based on steric hindrance caused by the density of polynucleotides. In aspects where interaction of polynucleotides with a biomolecule and/or non-biomolecule that are otherwise precluded by steric hindrance is desirable, the density of polynucleotides in the nanoconjugate is decreased to allow the biomolecule and/or non-biomolecule to interact with the polynucleotide.

It is also contemplated that polynucleotide surface density modulates the stability of the polynucleotide associated with the nanoparticle. Thus, in one embodiment, a nanoparticle comprising a polynucleotide is provided wherein the polynucleotide has a half-life that is at least substantially the same as the half-life of an identical polynucleotide that is not part of a nanoparticle. In other embodiments, the polynucleotide associated with the nanoparticle has a half-life that is about 5% greater to about 1,000,000-fold greater or more than the half-life of an identical polynucleotide that is not part of a nanoparticle.

Methods of Detecting a Target Polynucleotide

The disclosure provides methods of detecting a target molecule comprising contacting the target molecule with a composition as described herein. The contacting results, in various aspects, in regulation of gene expression as provided by the disclosure. In another aspect, the contacting results in a detectable change, wherein the detectable change indicates the detection of the target molecule. Detection of the detectable label is performed by any of the methods described herein, and the detectable label can be on a molecule that is part of a metal-ligand complex, supramolecular complex, or nanoparticle, or can be on the target molecule.

Methods of Inhibiting Gene Expression

Additional methods provided by the disclosure include methods of inhibiting expression of a gene product expressed from a target polynucleotide comprising contacting the target polynucleotide with a composition as described herein, wherein the contacting is sufficient to inhibit expression of the gene product. Inhibition of the gene product results from the hybridization of a target polynucleotide with a composition of the disclosure.

It is understood in the art that the sequence of a polynucleotide that is part of a metal-ligand complex, supramolecular complex, or nanoparticle need not be 100% complementary to that of its target polynucleotide in order to specifically hybridize to the target polynucleotide. Moreover, a polynucleotide that is part of a metal-ligand complex, supramolecular complex, or nanoparticle may hybridize to a target polynucleotide over one or more segments such that intervening or adjacent segments are not involved in the hybridization event (for example and without limitation, a loop structure or hairpin structure). The percent complementarity is determined over the length of the polynucleotide that is part of the metal-ligand complex, supramolecular complex, or nanoparticle. For example, given a metal-ligand complex, supramolecular complex, or nanoparticle comprising a polynucleotide in which 18 of 20 nucleotides of the polynucleotide are complementary to a 20 nucleotide region in a target polynucleotide of 100 nucleotides total length, the polynucleotide that is part of the metal-ligand complex, supramolecular complex, or nanoparticle would be 90 percent complementary. In this example, the remaining non-complementary nucleotides may be clustered or interspersed with complementary nucleotides and need not be contiguous to each other or to complementary nucleotides. Percent complementarity of a polynucleotide that is part of a metal-ligand complex, supramolecular complex, or nanoparticle with a region of a target polynucleotide can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Methods for inhibiting gene product expression include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of a metal-ligand complex, supramolecular complex, or nanoparticle comprising a polynucleotide. In other words, methods provided embrace those which result in essentially any degree of inhibition of expression of a target gene product.

The degree of inhibition is determined in vivo from a body fluid sample or from a biopsy sample or by imaging techniques well known in the art. Alternatively, the degree of inhibition is determined in vitro in a cell culture assay, generally as a predictable measure of a degree of inhibition that can be expected in vivo resulting from use of a composition as described herein. It is contemplated by the disclosure that the inhibition of a target polynucleotide is used to assess the effects of the inhibition on a given cell. By way of non-limiting examples, one can study the effect of the inhibition of a gene product wherein the gene product is part of a signal transduction pathway. Alternatively, one can study the inhibition of a gene product wherein the gene product is hypothesized to be involved in an apoptotic pathway.

It will be understood that any of the methods described herein can be used in combination to achieve a desired result. For example and without limitation, methods described herein can be combined to allow one to both detect a target polynucleotide as well as regulate its expression. In some embodiments, this combination can be used to quantitate the inhibition of target polynucleotide expression over time either in vitro or in vivo. The quantitation over time is achieved, in one aspect, by removing cells from a culture at specified time points and assessing the relative level of expression of a target polynucleotide at each time point. A decrease in the amount of target polynucleotide as assessed, in one aspect, through visualization of a detectable label, over time indicates the rate of inhibition of the target polynucleotide.

Thus, determining the effectiveness of a given polynucleotide to hybridize to and inhibit the expression of a target polynucleotide, as well as determining the effect of inhibition of a given polynucleotide on a cell, are aspects that are contemplated.

EXAMPLES

Example 1

Synthesis of Phosphoramidite Ligand Precursor

Phosphoramidite ligand precursor (3) was obtained in three steps starting from maltol, an inexpensive flavoring agent, as shown in the following scheme.

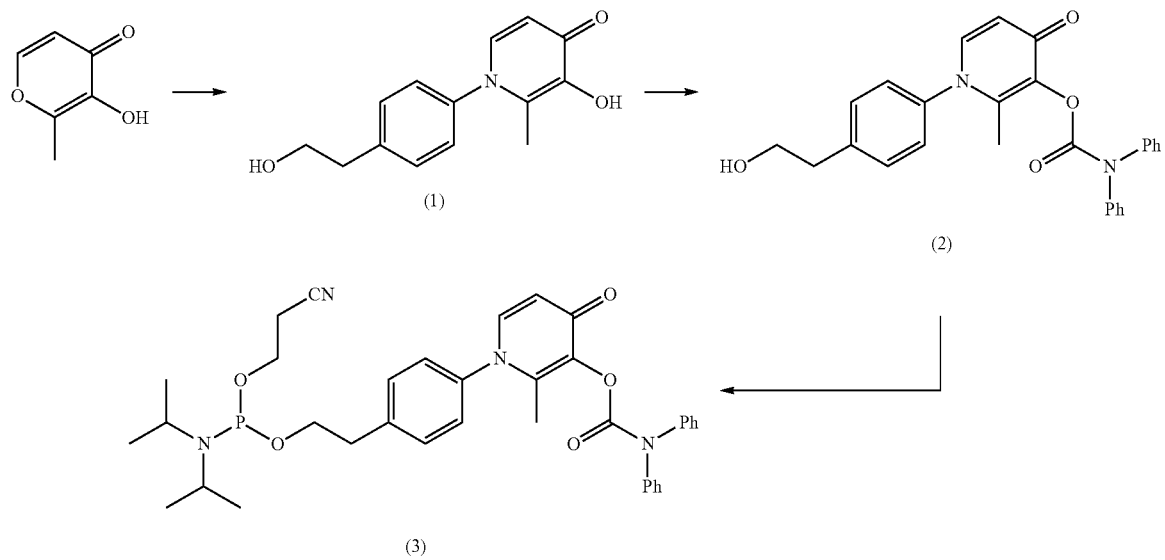

Synthesis of 1-(4'-(2-hydroxyethyl)phenyl)-2-methyl-3-hydroxy-4-pyridinone (1): To a 100 mL round-bottomed flask with a magnetic stirrer was added maltol (3.00 g, 23.8 mmol), 4-aminophenethyl alcohol (6.53 g, 47.6 mmol), and 25 mL dilute HCl (0.25N). The mixture was heated and refluxed for 24 hr with stirring, resulting in the precipitation of the desired product. Upon cooling to room temperature, the reaction mixture was diluted with $H_2O$ and vacuum-filtered to recover the precipitate. The filter cake was washed with $H_2O$ followed by methanol and allowed to dry on the filter, yielding 5.19 g (21.2 mmol, 90%) of 1-(4'-(2-hydroxyethyl)phenyl)-2-methyl-3-hydroxy-4-pyridinone (1) as a tan, microcrystalline powder. Crystals suitable for X-ray diffraction analysis were obtained by recrystallization from hot DMF. $^1$H NMR (400 MHz, DMSO-$d_6$) δ 7.48 (d, J=7.3 Hz, 1H), 7.37 (d, J=8.5 Hz, 2H), 7.30 (d, J=8.4 Hz, 2H), 6.16 (d, J=7.3 Hz, 1H), 3.63 (t, J=6.8 Hz, 2H), 2.78 (t, J=6.8 Hz, 2H), 1.93 (s, 3H). $^{13}$C NMR (101 MHz, DMSO-$d_6$) δ 169.98, 145.45, 141.28, 140.03, 138.38, 130.46, 129.13, 127.03, 111.24, 62.13, 38.80, 13.81. HRMS-EI (m/z): [M+H]$^+$ calculated for $C_{14}H_{16}NO_3$ 246.1125. found 246.1130.

Synthesis of diphenylcarbamoyl-protected pyridinone (2): To a 100 mL round-bottomed flask with a magnetic stirrer was added (1) (2.00 g, 8.15 mmol) followed by diphenylcarbamoyl chloride (2.08 g, 8.97 mmol) and dry pyridine (25 mL). The resulting suspension was stirred under $N_2$ and N,N-diisopropylethylamine (1.56 mL, 8.97 mmol) was added dropwise via syringe. After stirring overnight, the reaction mixture was poured into 200 mL dilute HCl (1M) and the resulting suspension vacuum-filtered and dried in vacuo to afford a brown solid. The crude product thus obtained was suspended in methylene chloride (10 mL) and shaken vigorously. The suspension was suction-filtered and washed with additional methylene chloride to afford 2.59 g of diphenylcarbamoyl-protected pyridinone (2) as an off-white powder (5.88 mmol, 72%). $^1$H NMR (400 MHz, DMSO-$d_6$) δ 7.63 (d, J=7.6 Hz, 1H), 7.50-7.15 (m, 14H), 6.22 (d, J=7.6 Hz, 1H), 4.67 (s, 1H), 3.62 (t, J=6.6 Hz, 2H), 2.76 (t, J=6.8 Hz, 2H), 1.90 (s, 3H). $^{13}$C NMR (101 MHz, DMSO-$d_6$) δ 170.48, 151.82, 150.04, 142.94, 141.65, 141.38, 141.12, 140.04, 139.47, 136.54, 130.63, 129.46, 127.47, 127.11, 126.82, 124.33, 115.82, 62.09, 38.80, 14.68. HRMS-EI (m/z): [M+H]$^+$ calculated for $C_{27}H_{25}N_2O_4$ 441.1809. found 441.1811.

Synthesis of diphenylcarbamoyl-protected pyridinone phosphoramidite (3): In an oven-dried 50 mL Schlenk flask with a magnetic stirrer was suspended (2) (0.500 g, 1.14 mmol) in 5 mL dry, degassed methylene chloride. The mixture was stirred under $N_2$ and N,N-diisopropylethylamine (0.59 mL, 3.41 mmol) was added via syringe, followed by O-cyanoethyl-N,N-diisopropylchlorophosphoramidite (0.51 mL, 2.27 mmol). After 1 hr, methanol (0.1 mL) was added and the mixture stirred for an additional 30 min. Solvent was removed by rotary evaporation and the crude product purified by column chromatography on silica gel, eluting with 3:1 acetone/CHCl$_3$ containing 1% triethylamine (v/v). Fractions containing the desired product (Rf~0.75) were pooled and evaporated to afford 0.53 g diphenylcarbamoyl-protected pyridinone phosphoramidite (3) (0.82 mmol, 73%) as a colorless foam. Prior to DNA synthesis, (3) was dissolved in anhydrous acetonitrile at a concentration of 0.1M and stored overnight at −20° C. over 3 Å molecular sieves. $^1$H NMR (400 MHz, CD$_2$Cl$_2$) δ 7.61-7.03 (m, 14H), 6.38 (d, J=7.6 Hz, 1H), 3.99-3.83 (m, 2H), 3.83-3.70 (m, 2H), 3.57 (dtd, J=13.6, 6.8, 3.3 Hz, 2H), 2.99 (t, J=6.5 Hz, 2H), 2.60 (t, J=6.3 Hz, 2H), 2.00 (s, 3H), 1.14 (dd, J=16.8, 6.8 Hz, 12H). $^{31}$P{$^1$H} NMR (162 MHz, CD$_2$Cl$_2$) δ 147.71. HRMS-EI (m/z): [M+H]$^+$ calculated for $C_{36}H_{42}N_4O_5P$ 614.2901. found 641.2897.

Example 2

Coupling of Ligand Phosphoramidite to Oligonucleotides & Purification of Modified Oligonucleotides A stock solution of phosphoramidite (3) was prepared by dissolving the dried amidite in anhydrous acetonitrile (0.8 mL MeCN per 100 μmol amidite). Due to the air and water sensitivity of the phosphoramidite, it is advised to prepare it immediately prior to DNA synthesis. Oligonucleotides were synthesized on a BioAutomation MerMade MM48 DNA synthesizer according to the standard 1 μmol, trityl-off protocol. All DNA synthesis reagents were obtained from Glen Research and used as received. The following two complementary 20-mers were designed:

5'-CCCAGCCTTCCAGCTCCTTG-3' (SV1) (SEQ ID NO: 1)

5'-CAAGGAGCTGGAAGGCTGGG-3' (SV2) (SEQ ID NO: 2)

Freshly-synthesized oligonucleotides, still attached to the solid support, were treated with 400 μL phosphoramidite solution and 600 μL Glen Research "Activator" solution (0.25M 5-ethylthiotetrazole in acetonitrile) and allowed to stand for 4 hr under $N_2$. The solid supports were then washed with 5 mL acetonitrile, oxidized with 1 mL Glen Research "Oxidizer" solution (0.02M iodine in THF/pyridine/$H_2O$), washed with 5 mL pyridine/MeCN (1:1), and finally rinsed with 10 mL acetonitrile and allowed to dry in vacuo. Oligonucleotides were deprotected and cleaved from the solid support by treating with saturated aqueous ammonium hydroxide for 16 hr at 55° C. Excess ammonia was removed under a stream of $N_2$, and the crude oligonucleotides were resuspended in Nanopure water and micron-filtered to remove the solid support beads.

The resulting oligonucleotide solutions were purified via reversed-phase HPLC (DynaMax Microsorb 300-10 C18 column), employing an elution gradient of 0-45% acetonitrile/tetraethylammonium acetate buffer over 45 minutes. Late-eluting fractions were collected and lyophilized to afford modified oligonucleotides (SV1-L) and (SV2-L), which were resuspended in Nanopure water and characterized by MALDI-TOF. Calc'd for (SV1-L): 6272 Da. Found: 6275 Da; Calc'd for (SV2-L): 6579 Da. Found: 6576 Da. Average yield of modified oligonucleotides, assuming 1 μmol theoretical yield per column, was approximately 25%. For example, when 4×1 μmol columns of (SV1-L) and (SV2-L) were synthesized, purified, and resuspended, the concentrations of the 1-mL stock solutions obtained were 1.06 mM for (SV1-L) and 1.11 mM for (SV2-L), corresponding to isolated yields of 26.5% and 27.8%, respectively.

Example 3

Metallation of Modified Single-Stranded Oligonucleotides

The quality of the modified oligonucleotides was assessed by observing their complexation reaction with iron(III). Fe(NO$_3$)$_3$.9H$_2$O was found to be a suitable iron precursor for all experiments involving metallation of oligonucleotides. First, a concentrated stock solution of oligonucleotide was standardized by appropriately diluting several aliquots, measuring their absorbance at 260 nm, and calculating the DNA concentration using the Beer-Lambert formula A=εcl. For (SV1-L), $\epsilon_{260}$=171200 L mol$^{-1}$ cm$^{-1}$; for (SV2-L), $\epsilon_{260}$=204200 L mol$^{-1}$ cm$^{-1}$. The ligand-metal charge transfer (LMCT) band which appeared in the visible spectrum upon formation of the tris-iron complex had an absorbance maximum ($\lambda_{max}$) at 460 nm with an associated extinction coefficient $\epsilon_{460}$ of 5700 L mol$^{-1}$ cm$^{-1}$.

A 100 μM solution of (SV1-L) or (SV2-L) in 1 mL of 1× phosphate-buffered saline was treated with 33 μM Fe$^{3+}$ and allowed to equilibrate overnight. Iron-binding was verified visually by the change in color of the solution. Kinetics experiments indicated that a ligand-modified 20-mer oligonucleotide completely complexed iron after standing 16 hr at room temperature in PBS buffer. The UV-Vis spectrum of the solution exhibited a LMCT band with an intensity of approximately 0.19 AU, corresponding to a Fe(DNA)$_3$ concentration of 33 μM. This value can vary depending on the purity of the oligos. It is important to maintain the pH of the oligonucleotide solution between 7-10, as this favors the tris-iron complex.

Example 4

Polymerization of Modified Oligonucleotides to Form Nanoparticles

Figure 1B:
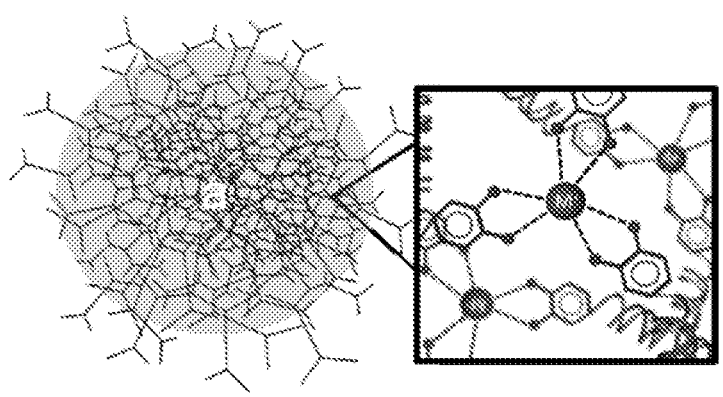
FIG. 1B is a schematic diagram of a supramolecular complex.

When the complementary strands (SV1-L) and (SV2-L) were allowed to hybridize, doubly terminally-modified duplexes were obtained. Melting experiments show that the SV1-L.SV2-L duplex possessed a melting temperature (Tm) of approximately 70° C. in 1× phosphate-buffered saline. Thus, at room temperature the duplex is stable and exists entirely in hybridized form. This monomer was then treated with $Fe^{3+}$ to induce formation of coordination polymer nanoparticles as shown in FIGS. 1A and 1B. The general procedure was as follows: a 1-mL stock solution of (SV1-L) and (SV2-L) was prepared in 1×PBS buffer containing 25 μM of each oligo, affording 25 μM of the iron-binding duplex (50 μM total DNA concentration). An aliquot of this solution was transferred to a 40 μL small-volume cuvette and analyzed by dynamic laser light scattering (DLS) to verify the sole presence of duplex DNA without larger aggregates. A stock solution of $Fe(NO_3)_3 \cdot 9H_2O$ was prepared by dissolving the iron salt in Nanopure water to give a final concentration of 0.01 M. This solution was also analyzed by DLS to ensure the absence of particulates. The iron stock solution was then added to the DNA solution to a total concentration of 33 μM and after each addition, the reaction mixture was vortexed and allowed to react overnight. Once the reaction was complete as determined by UV-Vis, the mixture was analyzed by DLS to confirm formation of aggregates.

The DNA nanoparticles thus obtained were purified by size-exclusion chromatography with Sepharose gel. For a 1 mL sample containing 100 μM DNA, approximately 3 mL of Sepharose CL-4B was employed as the solid phase. The Sepharose gel was first equilibrated in 1×PBS buffer by eluting 3-5 mL of the buffer solution. The DNA particle sample was then allowed to pass through the column and 500 μL fractions are collected. Each fraction was analyzed by DLS. Fractions containing particles of the desired size were collected and stored at 5° C., being indefinitely stable under these conditions.

Figure 2:
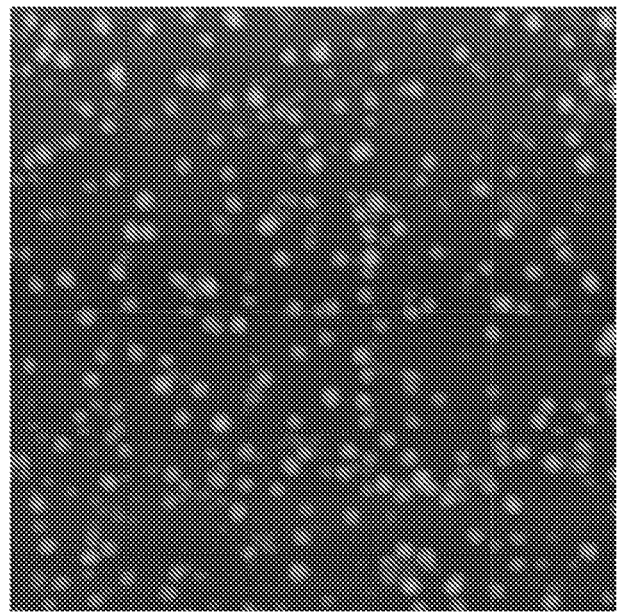
FIG. 2 is an atomic force microscopy (AFM) image of supramolecular complexes.

The nanoparticles were further characterized by atomic force microscopy. The particle sample in PBS buffer was deposited on freshly cleaved mica pre-treated with 10 mM $MgCl_2$. The mica surface was washed repeatedly with distilled $H_2O$ to remove buffer salts and unbound oligonucleotides, and then dried under a stream of $N_2$. AFM images were most easily obtained by tapping mode in air, and as shown in FIG. 2, revealed the presence of spherical particles having a size distribution nearly identical to that observed with DLS.

Example 5

Transfection and Imaging of Cells with Fluorescent DNA Coordination Polymer Particles To test for cell uptake, nanoparticles must be synthesized with dye-labeled oligonucleotides. Oligonucleotides are most easily labeled at the 3' terminus by using commercially-available fluorophore-labeled solid supports. To obtain dye-labeled oligonucleotides, the DNA synthesis procedure described in Example 2 was modified by employing Glen Research 3'-(6-Fluorescein) CPG solid supports in the place of standard solid supports. (SV1-DL) was synthesized according to the standard 1 μmol, trityl-off protocol. The final phosphoramidite coupling and workup steps were carried out in identical fashion. The dye and ligand-bearing oligonucleotides exhibited increased retention time in reversed-phase HPLC due to the hydrophobicity of the additional fluorescein modification. The purified oligonucleotide was characterized by MALDI-TOF. Calc'd for (SV1-DL): 6846 Da. Found: 6839 Da.

Figure 3:
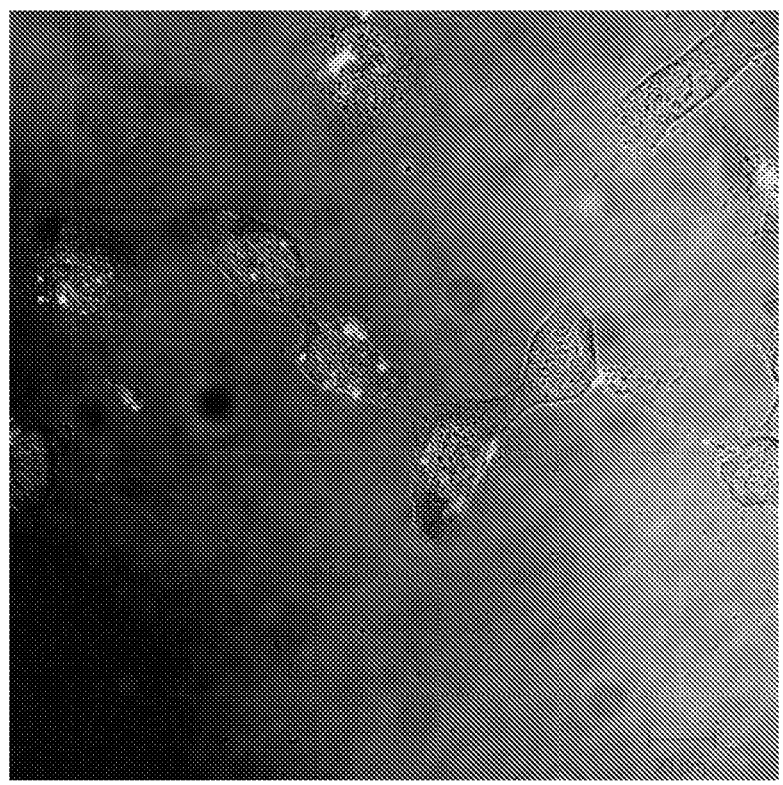
FIG. 3 is a confocal fluorescence microscopy image showing uptake by C166 mouse endothelial cells of supramolecular complexes containing fluorescein-labeled DNA.

Particles were grown in 1 mL of 1×PBS buffer at a total DNA concentration of 75 μM by portionwise addition of $Fe(NO_3)_3 \cdot 9H_2O$ to a solution of 50 μM (SV1-DL) and 25 μM (SV2-L). After allowing the particles to age overnight, C166 mouse endothelial cells were then incubated with 1 mL of cell culture medium containing the particle mixture at a total DNA concentration of 1 uM. After 24 hr, the cells were fixed, washed, and then examined by confocal fluorescence microscopy (exciting at 494 nm). As shown in FIG. 3, cell uptake of fluorescein-labeled DNA was observed, and images collected in Z-stack mode verified that the dye was present in the cytosol rather than the exterior of the cell membrane. The modified DNA was found to be nontoxic to cells under the conditions tested with no visible loss of cell viability after 24 hr.

Example 6

Regulation of Gene Expression

Figure 4:
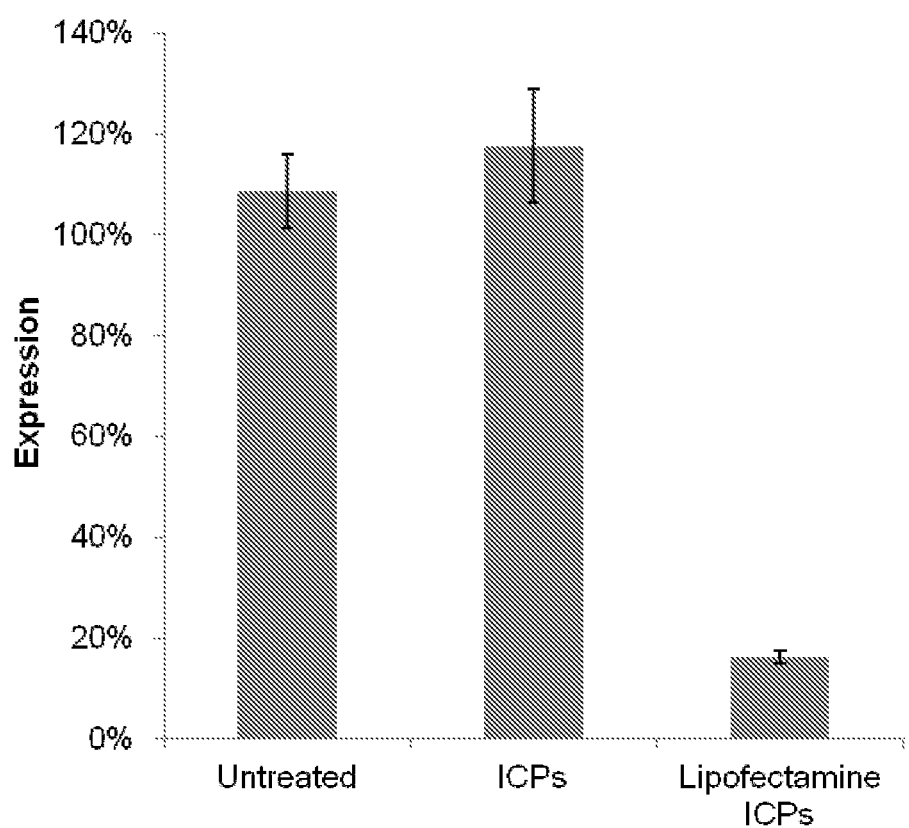
FIG. 4 is a graph showing levels of Survivin expression in skmel-28 cells.

The gene knockdown capability of the supramolecular complexes prepared in Example 4 ("ICP particles") was evaluated with skmel-28 human melanoma cells. Cells were cultured in Opti-MEM serum-free buffer, in 48-well plates with a density of 15,000 cells/well. Cells were then treated with ICP particles alone or ICP particles mixed with Lipofectamine® RNAiMAX (Invitrogen) according to manufacturer protocols to give a total DNA concentration of 30 nM. The cells were incubated for a total of 48 hours, replacing the media after 16 hours. Cells were then harvested and the total Survivin mRNA expression was quantitated by RT-qPCR, as shown in FIG. 4.

Example 7

Synthesis of Single-Stranded Oligodeoxyribonucleotides Modified with Ditopic 3-Hydroxy-4-Pyridinone Ligands Bis-3-hydroxy-4-pyridinone ligand (2b) was obtained in two steps starting from maltol as shown in the following scheme. 3,5-diaminobenzoic acid was purchased from TCI America; all other reagents were purchased from Sigma-Aldrich and used as received.

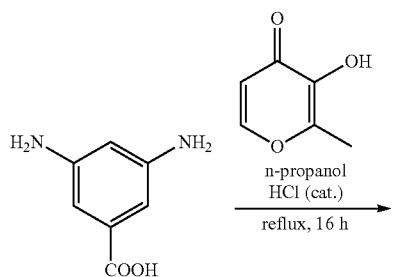

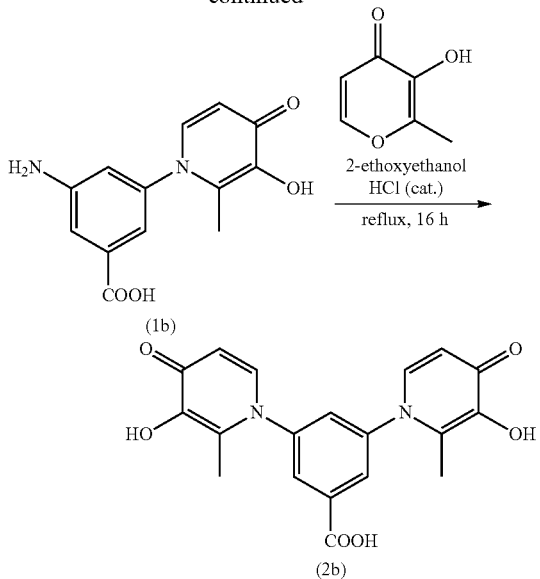

Diaminobenzoic acid mono-hydroxypyridinone (DABA-mono-HP) (1b): To a 100 mL round-bottomed flask with a magnetic stirrer was added 3,5-diaminobenzoic acid (5.00 g, 32.86 mmol), maltol (8.70 g, 69.00 mmol) and 30 mL of acidic n-propanol (49:1 propanol/12M HCl). The reaction vessel was fitted with a water-cooled condenser and the mixture heated to reflux for 16 h. The resulting suspension was filtered while hot and the solids washed with acetone (200 mL) to yield 4.84 g of diaminobenzoic acid mono-hydroxypyridinone (1b) as a tan powder (18.60 mmol, 57%). $^1$H NMR (400 MHz, DMSO-$d_6$) δ 7.52 (d, J=7.4 Hz, 1H), 7.28-7.26 (m, 1H), 6.92 (t, J=1.7 Hz, 1H), 6.67 (t, J=2.1 Hz, 1H), 6.16 (d, J=7.3 Hz, 1H), 5.77 (s, 2H), 1.96 (s, 3H). $^{13}$C NMR (101 MHz, DMSO-$d_6$) δ 169.94, 167.27, 150.62, 145.45, 142.79, 138.07, 133.24, 129.18, 115.64, 115.38, 114.35, 111.34, 40.33, 40.12, 39.91, 39.70, 39.49, 13.62. HRMS-ESI (m/z): [M+H]$^+$ calculated for $C_{13}H_{13}N_2O_4$ 261.0870. found 261.0875.

Diaminobenzoic acid bis-hydroxypyridinone (DABA-bis-HP) (2b): To a 100 mL round-bottomed flask with a magnetic stirrer was added diaminobenzoic acid mono-hydroxypyridinone (1b) (5.90 g, 22.67 mmol), maltol (3.57 g, 28.34 mmol), and 30 mL of acidic 2-ethoxyethanol (49:1 ethoxyethanol/12M HCl). The reaction vessel was fitted with a water-cooled condenser and the mixture heated to reflux for 16 h. The resulting suspension was filtered while hot and the solids washed with water (50 mL), followed by acetone (50 mL), to afford the crude product as a fine brown solid. The bis product was selectively isolated by trituration with hot pyridine (50 mL), filtration, and further trituration with hot dimethylformamide (50 mL) and drying in vacuo to afford 0.98 g of diaminobenzoic acid bis-hydroxypyridinone (2b) (2.66 mmol, 12%) as a grey powder sparingly soluble in methanol, soluble in DMSO and hot DMF. $^1$H NMR (400 MHz, DMSO-$d_6$) δ 8.03 (d, J=2.0 Hz, 2H), 8.00 (t, J=2.0 Hz, 1H), 7.64 (d, J=7.4 Hz, 2H), 6.22 (d, J=7.4 Hz, 2H), 2.02 (s, 6H). $^{13}$C NMR (126 MHz, TFA-d) δ 169.74, 167.16, 161.69, 145.89, 141.21, 136.89, 133.09, 113.84, 41.81, 36.12, 15.93. HRMS-ESI (m/z): [M+H]$^+$ calculated for $C_{19}H_{17}N_2O_6$ 369.1081. found 369.1084.

Conjugation of diaminobenzoic acid bis-hydroxypyridinone (2b) to DNA oligonucleotide: Oligonucleotides were synthesized on a BioAutomation MerMade MM48 DNA synthesizer according to the standard 1 μmol, trityl-on protocol. A 5-minute extended coupling time was employed for specialty phosphoramidites. All DNA synthesis reagents were obtained from Glen Research and used as received. The following amine-containing 20-mer was synthesized:

```
5'-Amino Modifier C12-CCCAGCCTTCCAGCTCCTTG-3'
(SV1-C12-NH2).
```

The solid support beads containing the completed oligonucleotide sequence were treated with 10 mL of deblocking solution (3% trichloroacetic acid in dichloromethane) to remove the monomethoxytrityl protecting group from the 5' amine terminus. The beads were then washed with acetonitrile (5 mL) and dried in vacuo. In a separate vial, 11.1 mg of diaminobenzoic acid bis-hydroxypyridinone (2b), 11.4 mg of HATU, and 17 μL of diisopropylethylamine were dissolved in 1 mL of DMSO and shaken for 5 minutes. As shown in the following scheme, this solution was then added to the DNA solid support beads and allowed to stand for 6 hours at room temperature. The solid support beads were washed with DMSO (5 mL) followed by acetonitrile (5 mL) and dried in vacuo.

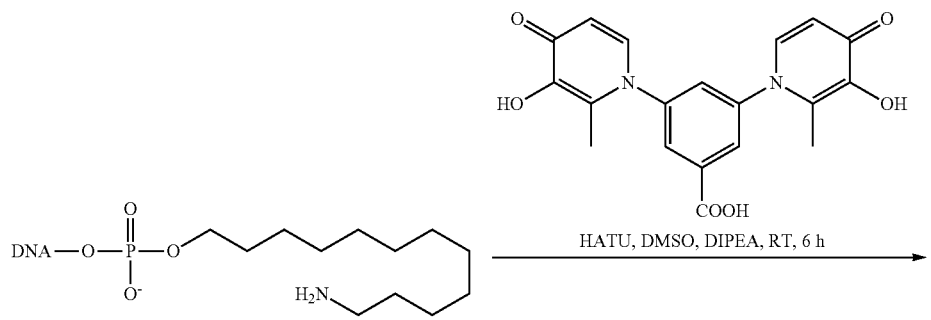

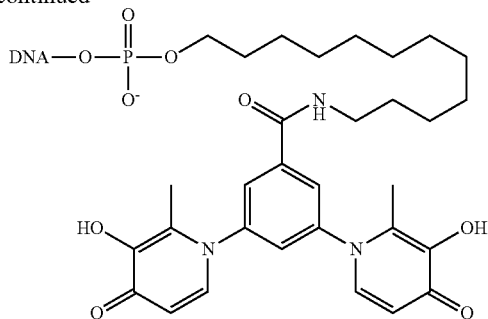

15

Oligonucleotides were deprotected and cleaved from the solid support by treating with saturated aqueous ammonium hydroxide for 16 hr at 55° C. Excess ammonia was removed under a stream of nitrogen, and the crude oligonucleotides were resuspended in deionized water and micron-filtered to remove the solid support beads. The crude product was characterized by MALDI-TOF and found to contain the desired oligonucleotide (SV1-C12-NH2-L). Calc'd: 6578 Da. Found: 6581 Da.

chloride octahydrate ($ZrOCl_2.8H_2O$) (21 mg, 0.066 mmol) was dissolved in 3 mL of DMF. The two solutions were mixed together in a 10 mL scintillation vial and acetic acid (300 µl) was added to the reaction mixture. The solution was heated at 90° C. for 18 h to yield UiO-66-$N_3$ ($Zr_6O_4OH_4$ ($C_8H_3O_4$—$N_3$)$_6$) MOF nanoparticles.

Synthesis of 19 nm UiO-66-$N_3$ ($Zr_6O_4OH_4(C_8H_3O_4$—$N_3)_6$) MOF nanoparticles: 19 nm UiO-66-$N_3$ MOF nanoparticles were synthesized according to the procedure

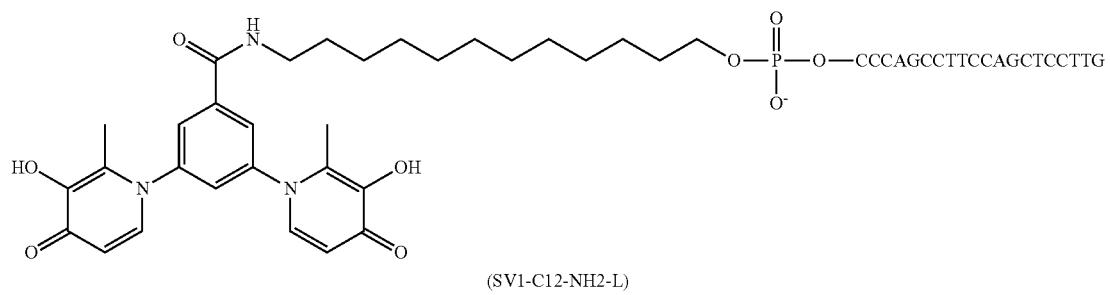

(SV1-C12-NH2-L)

Treatment of the crude oligonucleotide solution with an excess of ferric nitrate nonahydrate led to the appearance of the characteristic visible absorption band of the 3-hydroxy-4-pyridinone tris-$Fe^{3+}$ complex centered at λ=460 nm, further confirming successful modification of the oligonucleotide sequence. Purification was carried out by reversed-phase HPLC (DynaMax Microsorb 300-10 C18 column), with an elution gradient of 0-75% acetonitrile/tetraethylammonium acetate buffer over 45 minutes. The product displayed a retention time of ~20 minutes. Fractions were collected and lyophilized to yield purified (SV1-C12-NH2-L) as a white foam.

Example 8

Synthesis of Metal-Organic Framework Nanoparticles

All reagents were obtained from commercial sources (Alfa Aesar, Cambridge isotope laboratories, Sigma Aldrich, Glen Research, Spec Certi Corp) unless otherwise stated and were used without further purification. Ultrapure deionized water (18.2MΩ resistivity) from a Millipore system was used.

Synthesis of 14 nm UiO-66-$N_3$ ($Zr_6O_4OH_4(C_8H_3O_4$—$N_3)_6$) MOF nanoparticles: 2-Azido-1,4-benzenedicarboxylic acid (50 mg, 0.24 mmol) was dissolved in 1 mL of N,N-dimethylformamide (DMF). In a separate vial zirconyl described above for 14 nm UiO-66-$N_3$ MOF nanoparticles, except that 400 µl acetic acid was added.

Synthesis of 540 nm UiO-66-$N_3$ ($Zr_6O_4OH_4(C_8H_3O_4$—$N_3)_6$) MOF nanoparticles: 540 nm UiO-66-$N_3$ MOF nanoparticles were synthesized according to the procedure described above for 14 nm UiO-66-$N_3$ MOF nanoparticles, except that 3.5 mL acetic acid was added.

Figure 5:
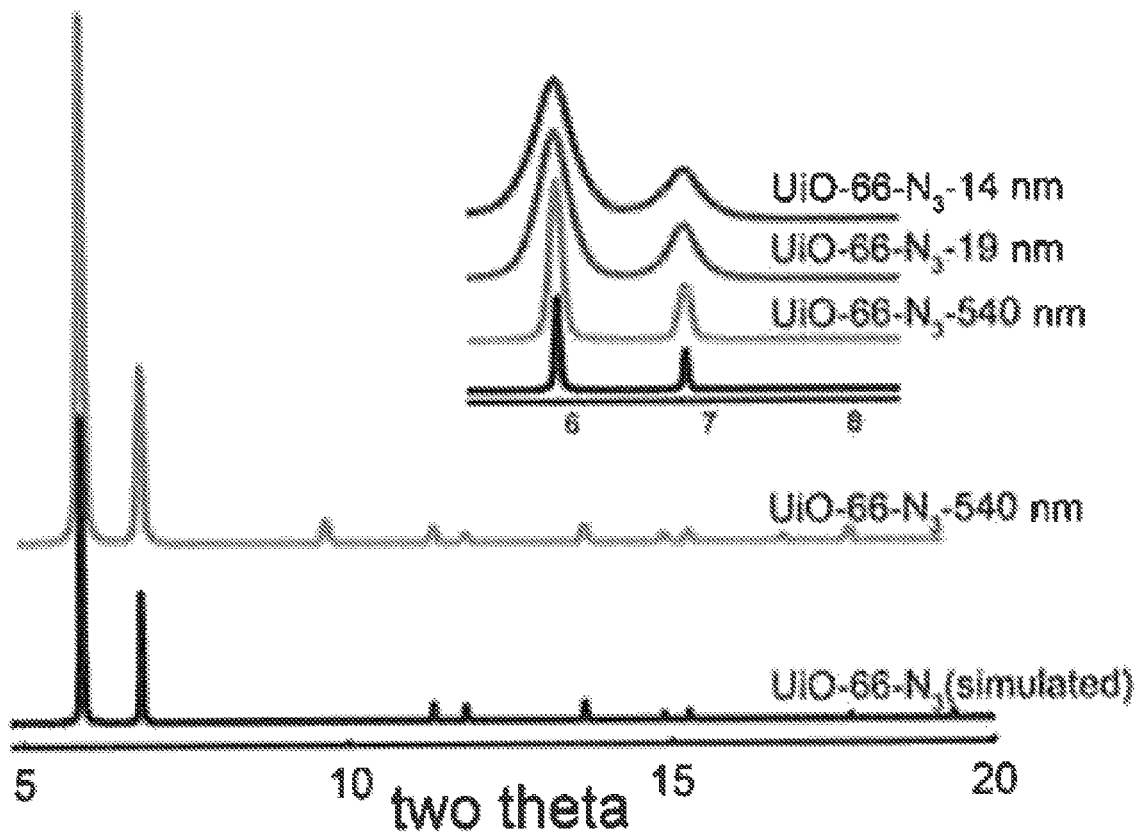
FIG. 5 is a graph showing powder X-ray diffraction (PXRD) of UiO-66-$N_3$ particles.
Figure 6A:
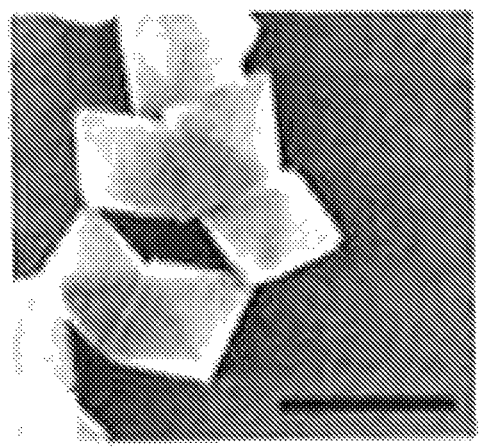
FIG. 6A is a scanning electron microscopy (SEM) image of 540 nm UiO-66-$N_3$ particles (scale bar=1 μm).
Figure 6B:
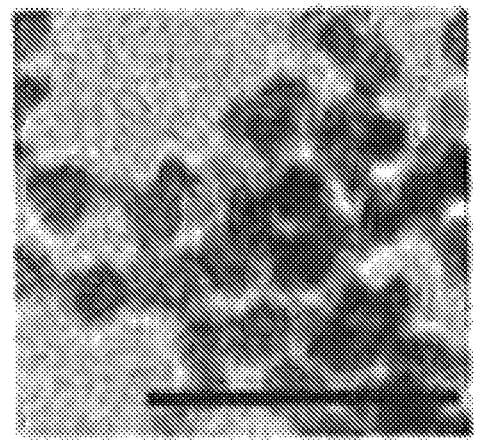
FIGS. 6B and 6C are transmission electron microscopy (TEM) images of 19 nm UiO-66-$N_3$ particles and 14 nm UiO-66-$N_3$ particles, respectively (scale bar=100 nm).
Figure 6C:
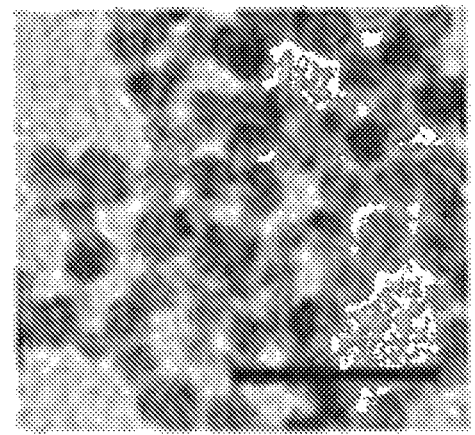

The MOF nanoparticles were characterized by powder X-ray diffraction (PXRD). As shown in FIG. 5, the PXRD of simulated UiO-66-$N_3$ particles was compared to the PXRD of synthesized 14 nm, 19 nm, and 540 nm UiO-66-$N_3$ particles. The MOF nanoparticles were also characterized by scanning electron microscopy (SEM) and transmission electron microscopy (TEM) as shown in FIG. 6.

Synthesis of Oligonucleotides: Oligonucleotides were synthesized using a Mermaid MM48 DNA synthesizer (Bio Automation) on a standard CPG solid phase support. Dibenzocyclooctyl (DBCO)-containing oligonucleotides were synthesized on a standard solid phase support using a DBCO-containing phosphoramidite (Glen Research). All oligonucleotides were deprotected under conditions recommended by the manufacturer and purified by reverse-phase high performance liquid chromatography (HPLC). Characterization and determination of concentration was determined by MALDI-TOF mass spectrometry and UV-Vis, respectively. The following oligonucleotides were synthesized ("DBCO" indicates that 5'-DBCO-TEG phosphoramidite (Glen Research) was used; "(T-DBCO)" indicates that DBCO-dT-CE phosphoramidite (Glen Research) was used:

```
3'-TTTTTTTTTT(T-TAMRA)TTTTTTTTTT-DBCO-5'
3'-TTTTTTTTTTTTTTTTTTTT(T-DBCO)-5'
3'-TTTTTTTTTTTTTTTTTTTT-DBCO-5'
3'-TTATAACTATTCCTAAAAAA-DBCO-5'
3'-TAGGAATAGTTATAAAAAAA-SH-5'
3'-TTTTTTTTTTTTTTTTTTTT-SH-5'.
```

Synthesis of Nucleic Acid-14 nm MOF Nanoparticle Conjugates: 14 nm UiO-66-N$_3$ MOF nanoparticles (0.15 nmol in 0.5 mL) were added to an aqueous solution of DNA (25 nmol in 0.5 mL) and mixed on a mechanical shaker for 72 h at 40° C. NaCl was added to the solution over six hours in three equal aliquots to a final concentration of 0.5 M. Free oligonucleotides were removed by centrifugation (3×15000 rpm for 90 minutes), followed by re-suspension of the nanoparticle oligonucleotide conjugates in H$_2$O for characterization and analysis.

Synthesis of Nucleic Acid-19 nm MOF Nanoparticle Conjugates: Nucleic acid-19 nm MOF nanoparticle conjugates were synthesized according to the procedure described above for nucleic acid-14 nm MOF nanoparticle conjugates, except that 0.08 nmol of 19 nm UiO-66-N$_3$ MOF nanoparticles were used.

Synthesis of Nucleic Acid-540 nm MOF Nanoparticle Conjugates: Nucleic acid-540 nm MOF nanoparticle conjugates were synthesized according to the procedure described above for nucleic acid-14 nm MOF nanoparticle conjugates, except that $8 \times 10^{-7}$ nmol of 540 nm UiO-66-N$_3$ MOF nanoparticles were used.

Figure 7:
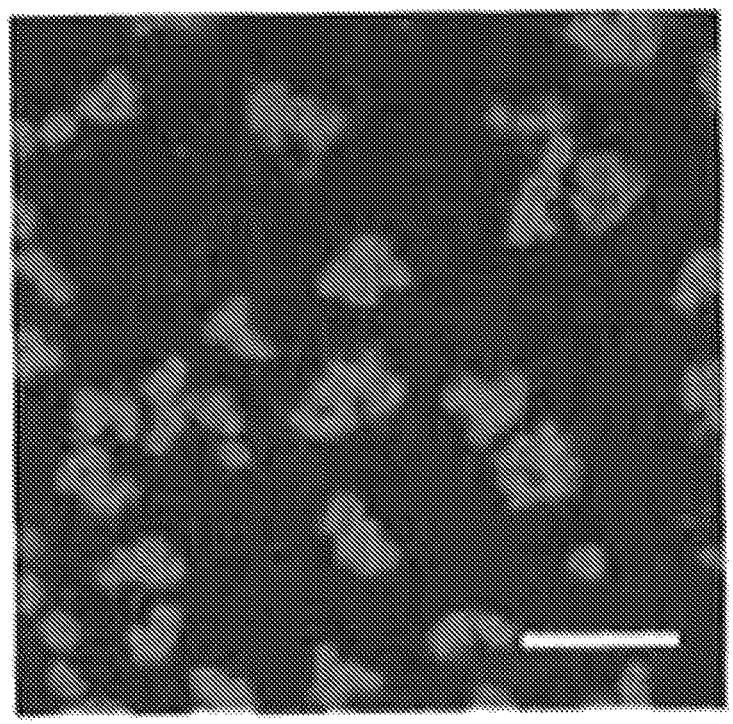
FIG. 7 is a confocal microscopy image of nucleic acid-540 nm MOF nanoparticle conjugates functionalized with TAMRA-labeled DNA (scale bar=10 μm).
Figure 8:
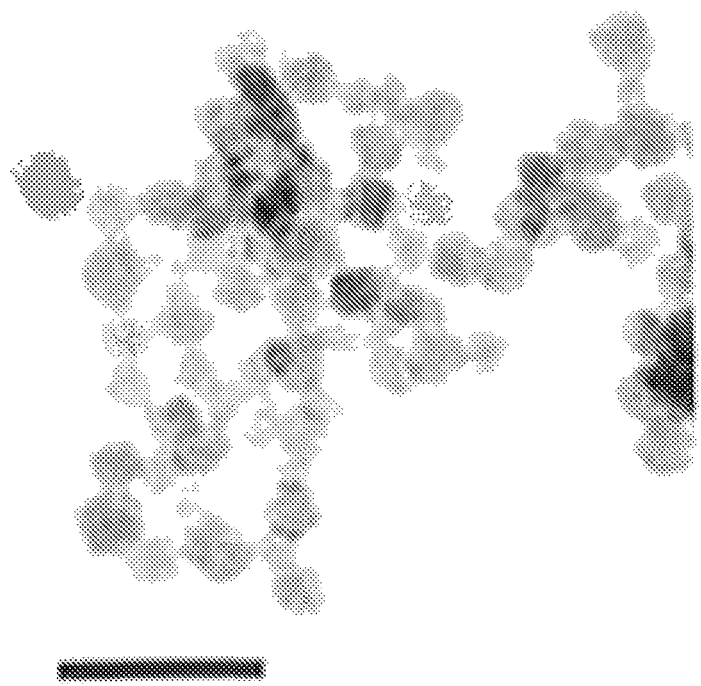
FIG. 8 is a transmission electron microscopy image of nucleic acid-19 nm MOF nanoparticle conjugates (scale bar=100 nm).
Figure 9:
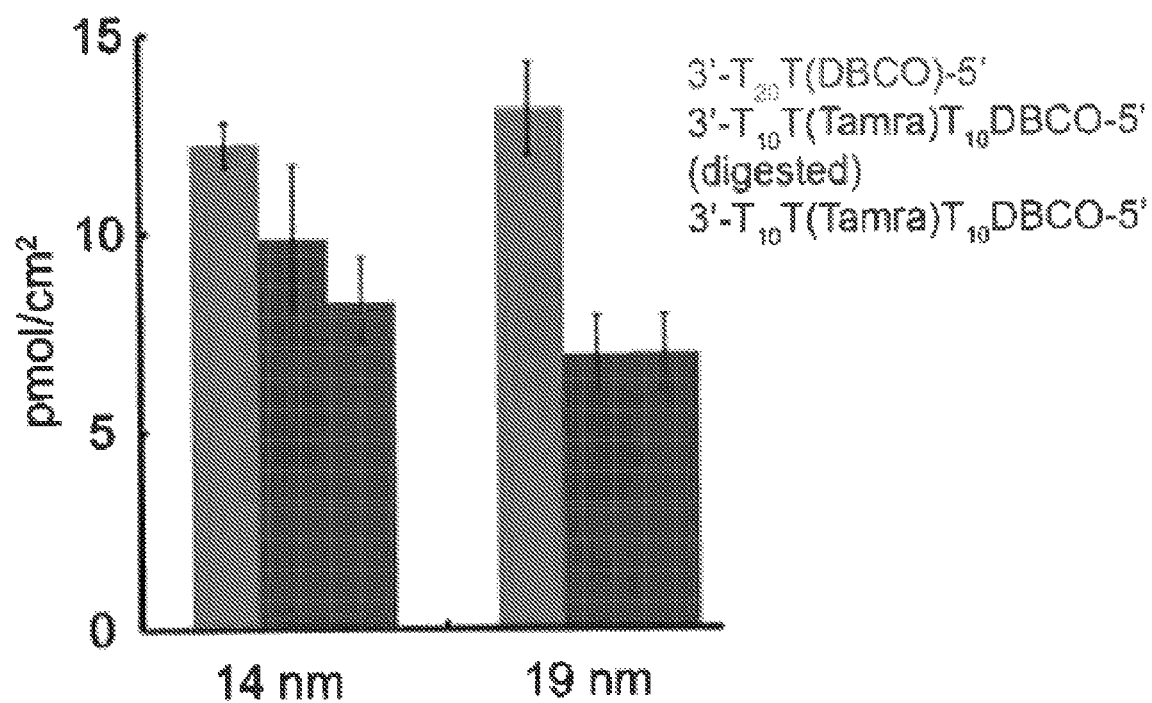
FIG. 9 is a graph showing the nucleic acid surface densities of nucleic acid-MOF nanoparticle conjugates.

Nucleic acid-540 nm MOF nanoparticle conjugates functionalized with TAMRA-labeled DNA were characterized by confocal microscopy, as shown in FIG. 7. Nucleic acid-19 nm MOF nanoparticle conjugates were characterized by transmission electron microscopy, as shown in FIG. 8. Nucleic acid surface densities of nucleic acid-14 nm MOF nanoparticle conjugates and nucleic acid-19 nm MOF nanoparticle conjugates are shown in FIG. 9. For each MOF particle size in FIG. 9 (14 nm or 19 nm), the left bar shows nucleic acid surface density determined by radiolabelling the 5' end of the 3'-T$_{20}$T(DBCO)-5' DNA., The middle and right bars for each MOF particle size in FIG. 9 (14 nm or 19 nm) show nucleic acid surface density determined by UV-Vis measurements of 3'-T$_{10}$T(TAMRA)T$_{10}$DBCO-5' DNA. The middle bar ("digested") shows nucleic acid surface density of samples digested in 0.1M NaOH prior to the UV measurement, which breaks down the MOF nanoparticle conjugate without altering the fluorescence of the TAMRA moiety.

Figure 10:
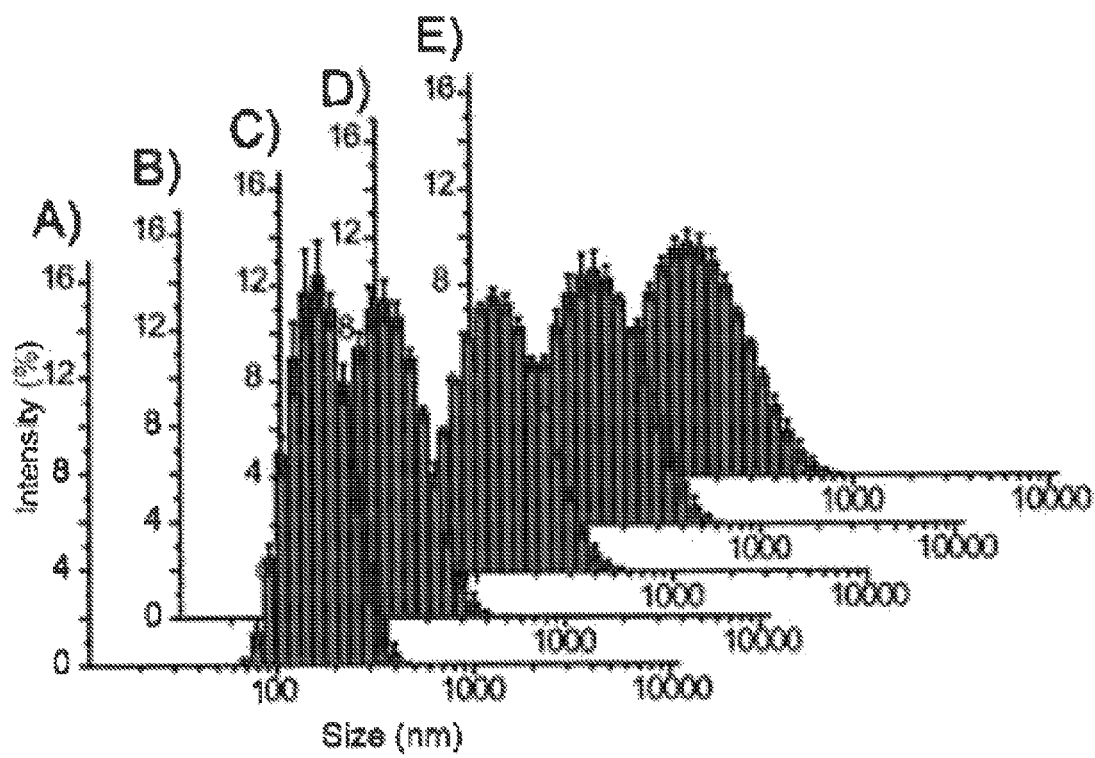
FIG. 10 is a series of graphs showing dynamic light scattering data for 14 nm MOF particles suspended in $H_2O$ (graph A), 14 nm MOF nanoparticle-DNA conjugates suspended in $H_2O$ (graph B), 14 nm MOF nanoparticle-DNA conjugates suspended in 0.1 M NaCl (graph C), 14 nm MOF nanoparticle-DNA conjugates suspended in 0.2 M NaCl (graph D), and 14 nm MOF nanoparticle-DNA conjugates suspended in 0.4 M NaCl (graph E).
Figure 11:
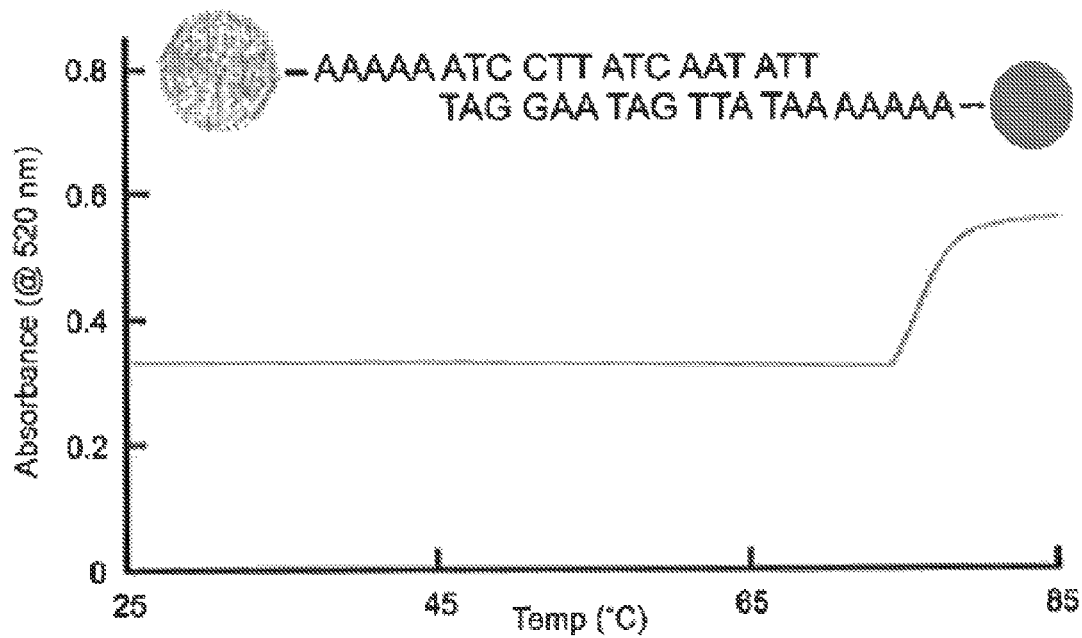
FIG. 11 is a graph showing melting analysis for MOF nanoparticle-DNA conjugates and gold nanoparticle DNA conjugates functionalized with complementary DNA.

The 14 nm MOF nanoparticles and nucleic acid-14 nm MOF nanoparticle conjugates were also characterized by dynamic light scattering as shown in FIG. 10. Melting analysis for the 14 nm MOF nanoparticle-DNA conjugates and gold nanoparticle DNA conjugates functionalized with complementary DNA is shown in FIG. 11.

Figure 12:
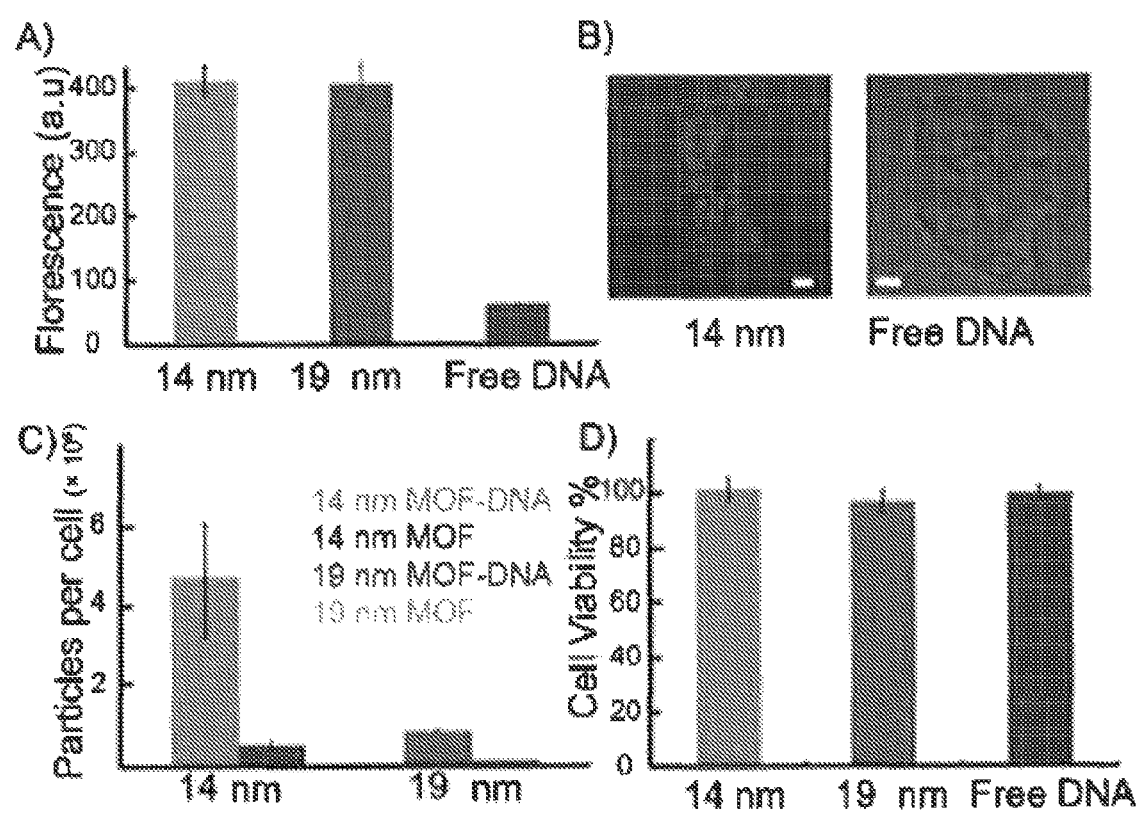
FIG. 12A is a graph showing cell uptake of MOF nanoparticle-DNA conjugates using flow cytometry.
FIG. 12B is a confocal microscopy image showing uptake by cells of 14 nm MOF nanoparticle-DNA conjugates (left panel) and free DNA (right panel) (scale bar=10 μm).
FIG. 12C is a graph showing nanoparticle uptake per cell of 14 nm MOF nano-particle-DNA conjugates (14 nm MOF-DNA), 14 nm MOF particles (14 nm MOF), 19 nm MOF nanoparticle-DNA conjugates (19 nm MOF-DNA), and 19 nm MOF particles.
FIG. 12D is a graph showing cell viability of cells contacted with 14 nm MOF nanoparticle-DNA conjugates, 19 nm MOF nanoparticle-DNA conjugates, and free DNA.

Uptake of the MOF nanoparticles and nucleic acid-MOF nanoparticle conjugates by HeLa cells was assessed by flow cytometry, confocal microscopy, and ICP-MS, as shown in FIG. 12. For quantitative uptake via flow cytometry (Guava Easycyte 8HT), HeLa cells were cultured on 13 mm diameter tissue culture coated slide covers and allowed to attach for 24 hours. HeLa cells were incubated with MOF nanoparticle DNA conjugates functionalized with TAMRA-labeled DNA for 24 h and directly compared to free TAMRA-labeled DNA at the same concentration (1 nM). Cells were washed with OptiMEM (Life Technologies) prior to imaging and confocal studies. Analogous procedures were followed for ICP-MS experiments; cells were treated with a solution containing $1 \times 10^{-7}$ mol/mL of Zr for both the unfunctionalized and functionalized MOF nanoparticles. ICP-MS was conducted by quantifying the number of cells contained in each well via flow cytometer, digesting the cell sample in nitric acid at 60° C. As shown in FIG. 12D, no significant cell toxicity was observed for the MOF-nanoparticle DNA conjugates.

REFERENCES

1. Cutler, J. I.; Auyeung, E.; Mirkin, C. A. Spherical Nucleic Acids. *J. Am. Chem. Soc.* 2012, 134, 1376-1391
2. Burgess, J.; Rangel, M. Hydroxypyridinones, hydroxypyranones, and their complexes. *Adv. Inorg. Chem.* 2008, 60, 167-243.
3. Liu, Z. D.; Hider, R. C. Design of iron chelators with therapeutic application. *Coordination Chem. Rev.* 2002, 232, 151-171
4. Tanaka, K.; Tengeiji, A.; Kato, T.; Toyama, N.; Shiro, M.; Shionoya, M. Efficient incorporation of a copper hydroxypyridone base pair in DNA. *J Am. Chem. Soc.* 2002, 124, 12494
5. Schlegel, M. K.; Zhang, L.; Pagano, N.; Meggers, E. Metal-mediated base pairing within the simplified nucleic acid GNA. *Org. Biomol. Chem.* 2009, 7, 476-482
6. Saghaie, L.; Sadeghi, M. M.; Nikazma, A. Synthesis, analysis and determination of partition coefficients of N-arylhydroxypyridinone derivatives as iron chelators. *Res. Pharm. Sci.* 2006, 1, 40-48
7. Takezawa, Y.; Maeda, W.; Tanaka, K.; Shionoya, M. Discrete self-assembly of iron(III) ions inside triple-stranded artificial DNA. *Angew. Chem. Int. Ed.* 2009, 48, 1081-1084
8. Ehrenschwender, T.; Barth, A.; Puchta, H.; Wagenknecht, H. A. Metal-mediated DNA assembly using the ethynyl-linked terpyridine ligand *Org. Biomol. Chem.* 2012, 10, 46-48
9. Choi, J. S.; Kang, C. W.; Jung, K.; Yang, J. W.; Kim, Y.-G.; Han, H. Synthesis of DNA triangles with vertexes of bis(terpyridine)iron(II) complexes *J. Am. Chem. Soc.* 2004, 126, 8606
10. Mitchell, N.; Ebner, A.; Hinterdorfer, P.; Tampé, R.; Howorka, S. Chemical tags mediate the orthogonal self-assembly of DNA duplexes into supramolecular structures. *Small* 2010, 6, 1732-1735
11. Megger, N.; Welte, L.; Zamora, F.; Müller, J. Metal-mediated aggregation of DNA comprising 2,2'-bipyridine nucleoside, an asymmetrically substituted chiral bidentate ligand. *Dalton Trans.* 2011, 40, 1802-1807

What is claimed:

1. A compound having a structure:

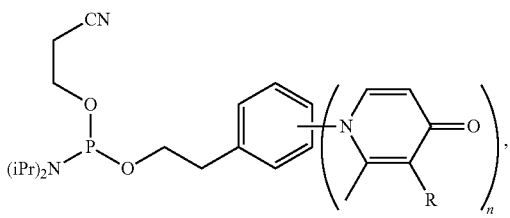

wherein R is OH or —O—C(O)—NAr$_2$, each Ar is aryl, and n is 1 or 2.

2. The compound of claim 1, wherein n is 1 and the pyridone moiety is attached to the phenyl at the para position.

3. The compound of claim 1, wherein n is 2 and the pyridone moieties are attached to the phenyl at the meta positions.

4. A polynucleotide comprising at a terminus a moiety comprising:

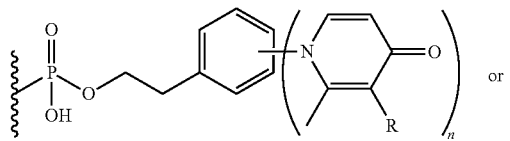 or

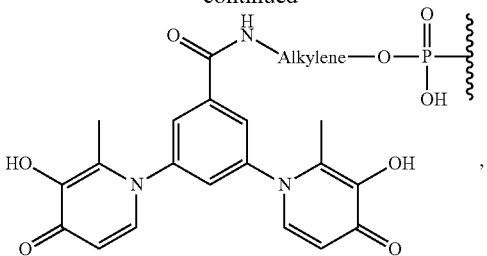

wherein R is OH or —O—C(O)—NAr$_2$, each Ar is aryl, n is 1 or 2, and Alkylene comprises 6-20 carbons.

5. The polynucleotide of claim 4, wherein n is 1 and the pyridone moiety is attached to the phenyl at the para position.

6. The polynucleotide of claim 4, wherein n is 2 and the pyridone moieties are attached to the phenyl at the meta positions.

7. A metal-ligand complex comprising the polynucleotide of claim 4 and iron (III).

8. A supramolecular complex comprising a first metal-ligand complex of claim 7 and a second metal-ligand complex of claim 7, wherein the first metal-ligand complex comprises a first polynucleotide and the second metal-ligand complex comprises a second polynucleotide that is sufficiently complementary to the first polynucleotide to hybridize under appropriate conditions.

9. A method of inhibiting expression of a gene product encoded by a target polynucleotide comprising contacting the target polynucleotide with the supramolecular complex of claim 8 under conditions sufficient to inhibit expression of the gene product.

* * * * *